(12) United States Patent
Haw et al.

(10) Patent No.: US 7,078,364 B2
(45) Date of Patent: Jul. 18, 2006

(54) SHIP-IN-A-BOTTLE CATALYSTS

(75) Inventors: James F. Haw, Altadena, CA (US); Weiguo Song, Alhambra, CA (US)

(73) Assignee: University of Southern California, Los Angeles, CA (US)

( * ) Notice: Subject to any disclaimer, the term of this patent is extended or adjusted under 35 U.S.C. 154(b) by 0 days.

(21) Appl. No.: 10/127,346

(22) Filed: Apr. 22, 2002

(65) Prior Publication Data

US 2002/0183577 A1 Dec. 5, 2002

Related U.S. Application Data

(60) Provisional application No. 60/311,324, filed on Aug. 10, 2001, provisional application No. 60/285,463, filed on Apr. 20, 2001.

(51) Int. Cl.
*B01J 27/182* (2006.01)
*B01J 27/14* (2006.01)
*B01J 29/00* (2006.01)

(52) U.S. Cl. .......................... 502/214; 502/62; 502/64; 502/71; 502/77; 502/85; 502/202; 502/208

(58) Field of Classification Search ................ 502/62, 502/64, 71, 77, 85, 202, 208, 214
See application file for complete search history.

(56) References Cited

U.S. PATENT DOCUMENTS

| | | | | |
|---|---|---|---|---|
| 3,982,912 | A | | 9/1976 | Yatsurugi et al. ............... 55/35 |
| 4,414,005 | A | * | 11/1983 | De Bievre et al. ............ 95/127 |
| 4,620,857 | A | | 11/1986 | Vansant et al. ................. 55/75 |
| 5,039,641 | A | * | 8/1991 | Vansant et al. ............... 502/85 |
| 5,089,244 | A | | 2/1992 | Parent et al. ................ 423/347 |
| 5,206,004 | A | | 4/1993 | Park ........................... 423/700 |
| 5,968,242 | A | * | 10/1999 | Holderich et al. ......... 106/31.6 |
| 6,807,535 | B1 | | 10/2004 | Goodkovsky .................. 706/3 |

FOREIGN PATENT DOCUMENTS

EP 0049936 4/1982 ..................... 19/4

OTHER PUBLICATIONS

Li et al.; "Light-emitting boron nitride nanoparticles encapsulated in zeolite ZSM-5"; Microporous and Mesoporous Materials, vol. 40; pp. 263-269; 2000, (no month).

Corma, A., Inorganic Solid Acids and Their Use in Acid-Catalyzed Hydrocarbon Reactions, *Chemical Reviews*, 1995, 95, 559-614.

Corma, A., From Microporous to Mesoporous Molecular Sieve Materials and Their Use In Catalysis, *Chemical Reviews*, 1997, 97, pp. 2373-2419.

VanSanten, R.A.; Kramer, G.J., Reactivity Theory of Zeolitic Bronsted Acidic Sites, *Chemical Reviews*, 1995, 95, pp. 637-660.

Stocker, M., Methanol-to Hydrocarbons: Catalytic Materials and Their Behavior, *Microporous and Mesoporous Materials*, 1999, vol. 29, pp. 3-48.

Keil, F.J., Methanol-to Hydrocarbons: Process Technology, *Microporous nd Mesoprous Materials*, 1999, vol. 29, pp. 49-66.

Dahl, I.M., Mostad, H.; Akporiaye, D.; Wendelbo, R. Structural and Chemical Influences on the MTO Reaction: a Comparison of Chabazite and SAPO-34 as MTO Catalysts, *Microporous and Mesoporous Materials*, 1999, vol. 29, pp. 185-190.

Ashtekar, S.; Chilukur, S.V.V.; Prakash, A.M..; Harendranath, C.S.; Chakrabarty, D.K., Small Pore Aluminum Phosphate Molecular-Sieves With Chabazite Structure - Incorporation of Cobalt in the Structures SAPO-34 and SAPO-44, *J. Phys. Chem.*, 1995, vol. 99, pp. 6937-6943.

Inoue, M.; Dhupatemiya, P.; Phatanari, S.; Inui, T. Synthesis Course of the Ni-SAPO-34 Catalyst for Methanol-to-Olefin Conversion, *Microporous and Mesoporous Materials*, 1999, vol. 28, pp. 19-24.

(Continued)

*Primary Examiner*—Elizabeth D. Wood

(57) ABSTRACT

In accordance with the present invention there is provided a novel catalyst system in which the catalytic structure is tailormade at the nanometer scale using the invention's novel ship-in-a-bottle synthesis techniques. The invention describes modified forms of solid catalysts for use in heterogeneous catalysis that have a microporous structure defined by nanocages. Examples include zeolites, SAPOs, and analogous materials that have the controlled pore dimensions and hydrothermal stability required for many industrial processes. The invention provides for modification of these catalysts using reagents that are small enough to pass through the windows used to access the cages. The small reagents are then reacted to form larger molecules in the cages.

12 Claims, 13 Drawing Sheets

OTHER PUBLICATIONS

Thomas, J.M.; Xu, Y.; Catlow, C.R.A.; Couves, J.W. Synthesis and Characterization of a Catalytically Active Nickel Silicoaluminophosphate Catalyst for the Conversion of Methanol to Ethene, *Chem. Mater*, 1991, vol. 3, pp. 667-672.

Kang, M.; Inui, T., Dynamic Reaction Characteristics Affected by Water Molecules During the Methanol to Olefin Conversion on NiAPSO-34 Catalysts, Journal of Molecular Catalysis a-Chemical, 1999, vol. 140, pp. 55-63.

Wilson, S.; Barger, P., The Characteristics of SAPO-34 Which Influence the Conversion of Methanol to Light Olefins, *Microporous and Mesoporous Materials*, 1999, vol. 29, pp. 117-126.

Dahl, I.M.; Kolboe, S., On the Reaction-Mechanism for Hydrocarbon Formation from Methanol Over SAPO-34 .1.Isotopic Labeling Studies of the Co-Reaction of Ethene and methanol, J. Catal., 1994, vol. 149, pp. 458-464.

Marchese, L.; Frache, A.; Gianotti, E.; Marta, G.; Causa, M.; Coluccia, S., ALPO-34 and SAPO-34, Synthesized by Using Morpholine as Templating Agent.FTIR and FT-Raman Studies of the Host-Guest and Guest-Guest Interactions Within the Zeolitic Framework, *Microporous and Mesoporous Materials*, 1999, vol. 30, pp. 145-153.

Prakash, A.M.; Unnikrishnan, S., Synthesis of SAPO-34 - High-Silicon Incorporation in the Presence of Morpholine as Template, Journal Chemical Society, Faraday Trans., 1994, vol. 90, pp. 2291-2296.

* cited by examiner

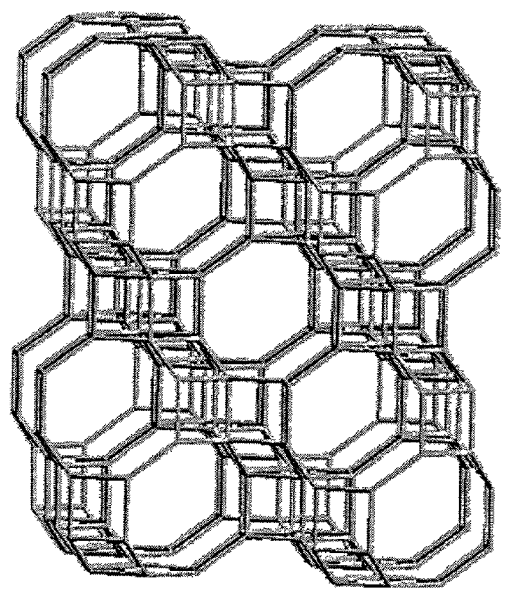
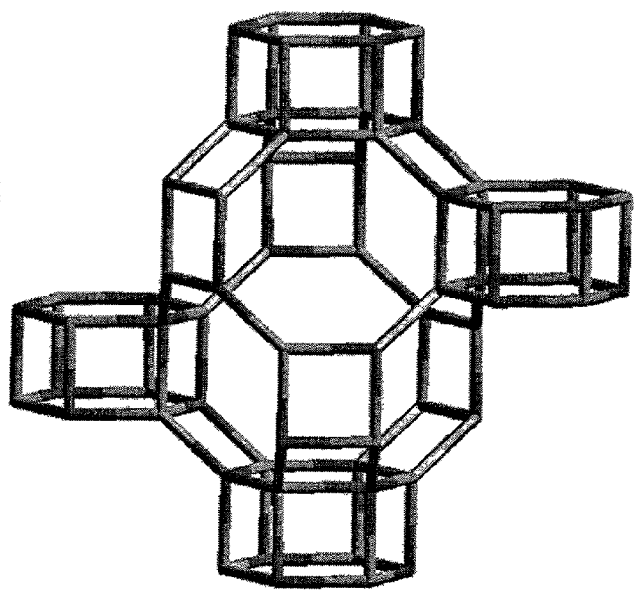
FIGURE 1A
FIGURE 1B

SHIP-IN-A-BOTTLE CATALYSTS

RELATED APPLICATION DATA

This application claims priority to U.S. Provisional Application Ser. No. 60/285,463, filed Apr. 20, 2001, now abandoned, and to U.S. Provisional Application Ser. No. 60/311,324, filed on Aug. 10, 2001, now abandoned, the disclosures of which are incorporated by reference herein.

RIGHTS OF FEDERAL GOVERNMENT

This work was supported by Department of Energy grant no. DE-FG03-93ER14354 and National Science Foundation grant no. CHE-9996109. The Federal Government may have certain rights in this invention.

FIELD OF THE INVENTION

This invention relates to solid catalysts. In particular, the invention relates to solid catalysts that contain a microporous framework. More particularly, the invention relates to novel SAPO catalysts.

BACKGROUND OF THE INVENTION

Control of selectivity is a central problem in catalysis, and this is particularly challenging with the microporous solid acid catalysts used in most industrial catalytic processes. Of particular interest here is methanol-to-olefin (MTO) catalysis, which has enormous commercial potential as discussed below.

Light olefins, defined herein as ethylene, propylene, and butylene, serve as feeds for the production of numerous chemicals. Olefins traditionally are produced by petroleum cracking. Because of the limited supply and/or the high cost of petroleum sources, the cost of producing olefins from petroleum sources has increased steadily. For example, the large increase in demand for polyethylene has nearly exceeded the capacity of refineries to produce ethylene as a byproduct of petroleum conversion to gasoline.

Therefore, there is a need for alternative feedstocks for the production of light olefins. Amongst such feedstocks are oxygenates, such as alcohols, particularly methanol, dimethyl ether, and ethanol. Alcohols may be produced by fermentation, or from synthesis gas derived from natural gas, petroleum liquids, carbonaceous materials, including coal, recycled plastics, municipal wastes, or any organic material. Consequently, because of the wide variety of Attorney Docket sources, alcohol, alcohol derivatives, and other oxygenates have promise as an economical, non-petroleum source for olefin production.

Methanol is a particularly attractive olefin feedstock because it can be produced from natural gas, mostly methane, which is so inexpensive near the well head that it is frequently vented or flared. Converting natural gas to methanol has the added advantage of reducing pollution because venting or flaring natural gas causes emissions of methane and $CO_2$, respectively, which are greenhouse gases. Further, methanol has the advantage that it, unlike natural gas, is easily transported using conventional tankers.

Because of the attractiveness of methanol as a potential olefin feedstock, there is intense developmental effort focused on converting methanol to olefins. Several major petrochemical companies are operating methanol-to-olefin (MTO) pilot plants, and large scale commercialization is expected in several years.

The catalysts used to promote the conversion of oxygenates to olefins are molecular sieve catalysts. For example, the earliest MTO processes were based on the aluminosilicate zeolite HZSM-5, a material with channels ca. 0.55 run in diameter. ZSM-5 has been extensively studied for the conversion of methanol to olefins. Unfortunately, ZSM-5 produces not only the desired light olefins, but also undesired by-products. In particular, ZSM-5 produces aromatics, particularly at high methanol conversion. Aromatics such as toluene and p-xylene readily diffuse through the ZSM-5 topology. At one time aromatics were used in gasoline fonnulations but arornatics are no longer desirable in US gasoline, and to serve as an MW catalyst, HZSM-5 must be modified to greatly reduce aromatic formation. This has been attempted, with some degree of success, by further restricting the channel size, usually by partial exchange with $Mg^{2+}$ or by adsorbing an organic phosphorus compound and calcining to leave some kind of phosphate debris in the channel.

The foregoing points to the need for MTO catalysts that do not produce large amounts of unwanted by-products, such as aromatics, methane, carbon monoxide, and hydrogen gas. Furthermore, because ethylene and propylene are the most sought after products of the MTO conversion reaction, there is a need for catalysts that are most selective to ethylene and/or propylene, and for methods for increasing the selectivity of the reaction to ethylene and/or propylene.

Towards that end, zeolites with a small pore size are being developed because such zeolites have a higher selectivity to lower alkenes, even at 100 mol % methanol conversion. However, even though small pore size zeolites have a higher selectivity to lower alkenes, there is a need to further tailor zeolites to achieve other process objective. For example, amongst lower alkenes, there is a need for catalysts that selectively produce ethylene over propylene or vice versa.

This invention provides catalysts that provide such desirable characteristics, and also provides novel methods for tailor-making catalysts with desirable properties.

SUMMARY OF THE INVENTION

This invention provides for nano-functionalization of catalysts to improve, inter alia, catalyst selectivity and yield. The invention provides new catalytic compositions of matter synthesized by ship-in-a-bottle routes.

In accordance with the present invention there is provided a novel catalyst system in which the catalytic structure is tailormade at the nanometer scale using the invention's novel ship-in-a-bottle synthesis techniques. The invention describes modified forms of solid catalysts for use in heterogeneous catalysis that have a microporous structure defined by nanocages. Examples include zeolites, SAPOs, and analogous materials that have the controlled pore dimensions and hydrothermal stability required for many industrial processes. The invention provides for modification of these catalysts using reagents that are small enough to pass through the windows used to access the cages. The small reagents are then reacted to form larger molecules in the cages.

In a preferred embodiment, the invention provides for materials and methods for increasing selectivity in methanol-to-olefin (MTO) catalysis. In another aspect, the invention provides methods for synthesizing olefins from oxygenate feedstock using the catalysts of the invention.

BRIEF DESCRIPTION OF THE DRAWINGS

FIG. 1. Illustrations of the chabazite (CHA) topology. FIG. 1A. (LEFT) Extended structure showing the interconnection of cages through narrow six-ring windows that are ca. 0.38 nm in diameter. FIG. 1B. (RIGHT) Expanded view emphasizing a cage, which is ca. 1.0 nm by 0.7 nm. SAPO-34 would be of this composition except with (typically) one substitution of Si for P per cage.

(B) The ethylene selectivity data in A plotted against Me$_{ave}$.

Figure 7:
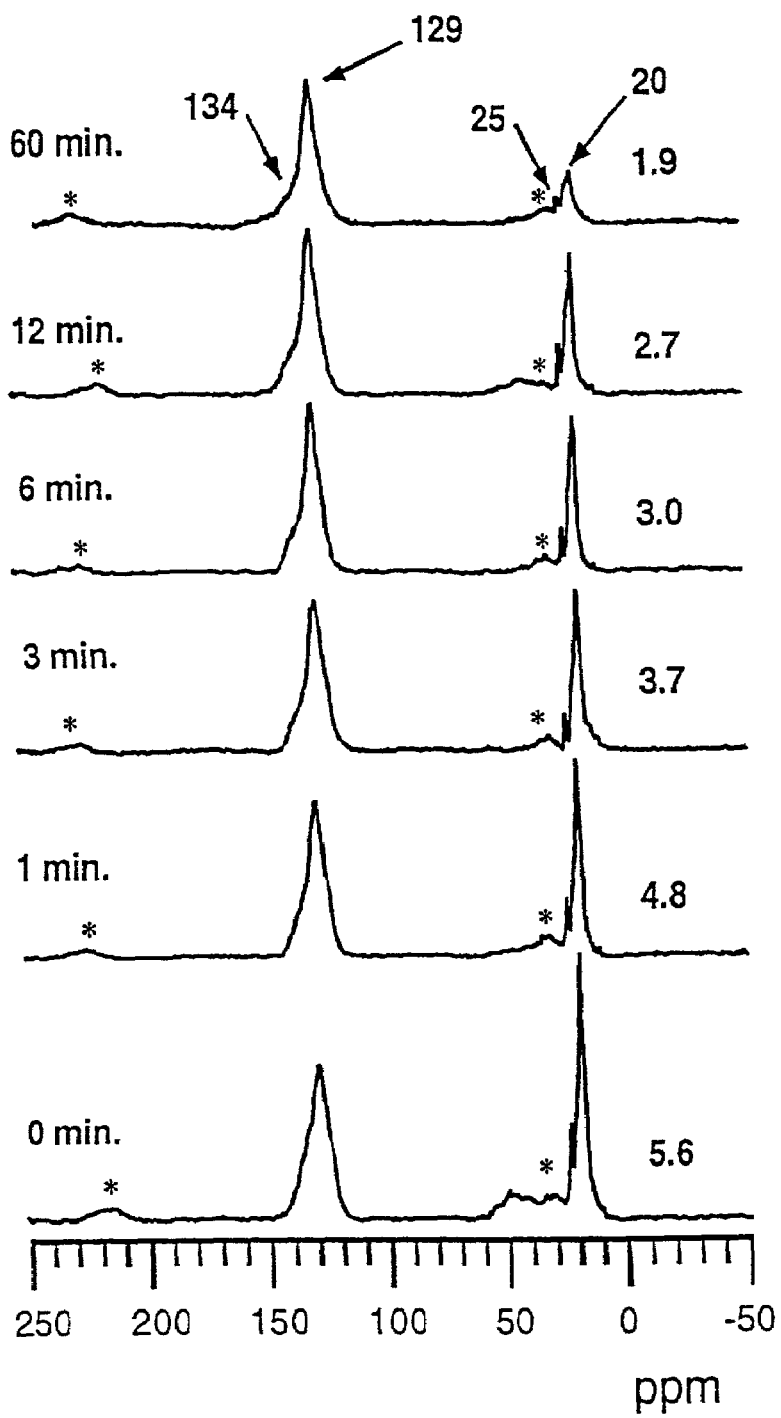
FIG. 7. 75 MHz $^{13}$C CP/MAS NMR spectra showing the loss of methyl groups as a function of time from methylbenzenes trapped in the HSAPO-34 nanocages at 400° C. For each case, a fresh catalyst bed was used to convert 0.1 mL of methanol-$^{13}$C at a WHSV of 8 h$^{-1}$, and then methanol flow was abruptly cut off. The catalyst bed was maintained at temperature with He flow (200 sccm) for the time indicated, and then the reactor temperature was rapidly quenched to ambient. Entire catalyst beds were loaded into MAS rotors to avoid sampling errors, and cross polarization spectra were measured at room temperature (2 ms contact time, 2000 scans). The average numbers of methyl groups per ring Me$_{ave}$, were calculated from Bloch decay spectra (90° pulse, 10 s delay) very similar to the cross polarization spectra shown.
Figure 11:
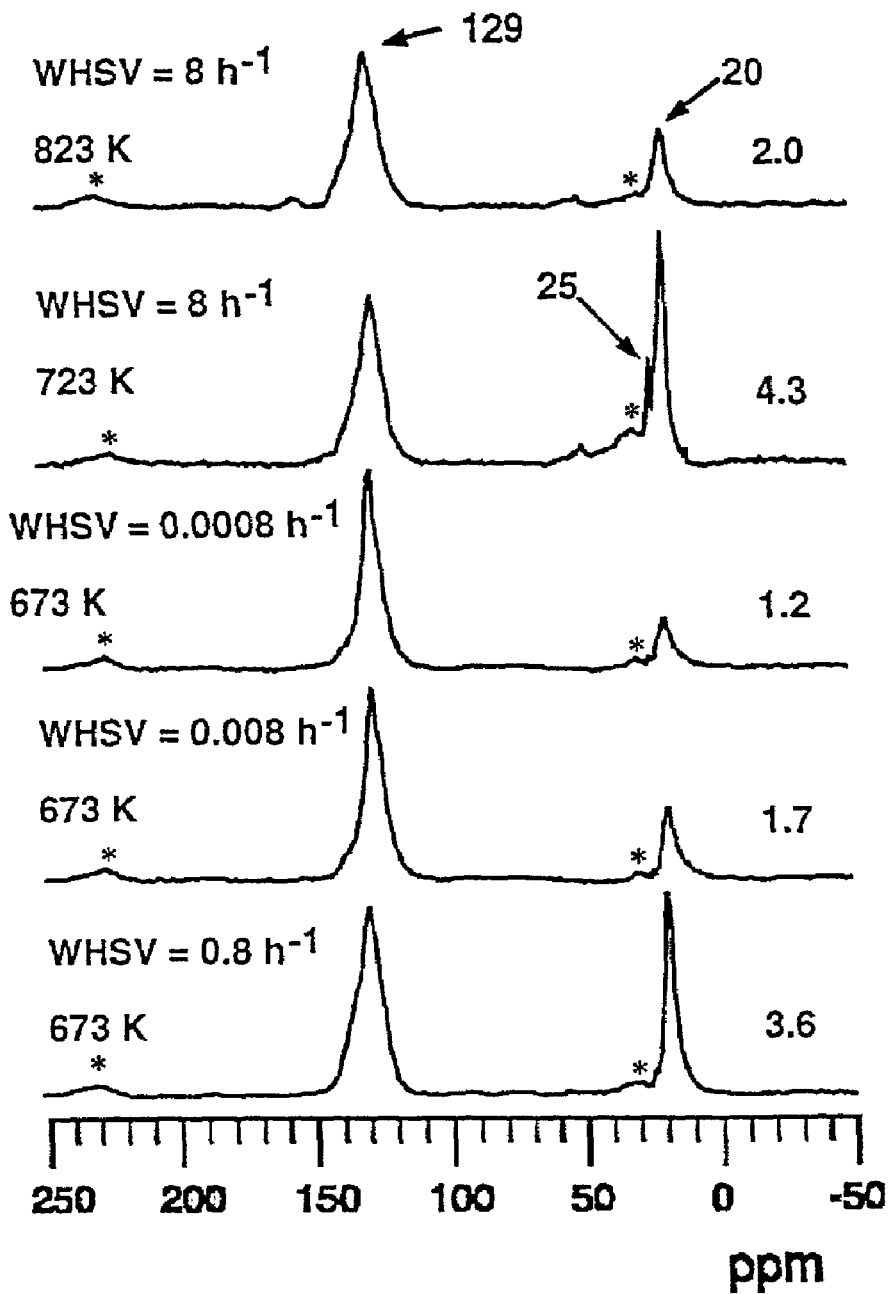

FIG. 11. 75 MHz $^{13}$C CP/MAS NMR spectra from experiments very similar to those in FIG. 7, except probing conditions intended to lower steady-state average numbers of methyl groups per ring. In each case, the thermal quench was performed immediately upon cessation of methanol-$^{13}$C flow. Lower space velocities or higher temperatures reduce the average number of methyl groups.

Figure 12:
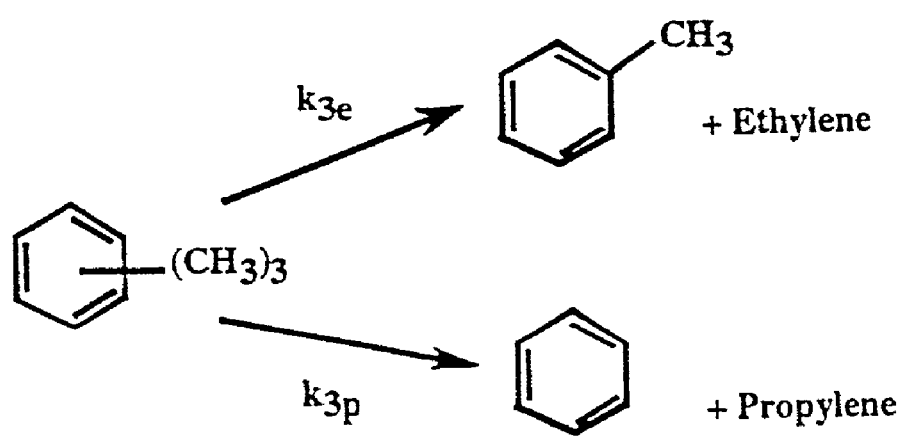

FIG. 12. The two possible unimolecular reactions of (isomer equilibrated) trimethylbenzene in an HSAPO-34 nanocage. The notation for the rate constants is illustrated.

Figure 13:
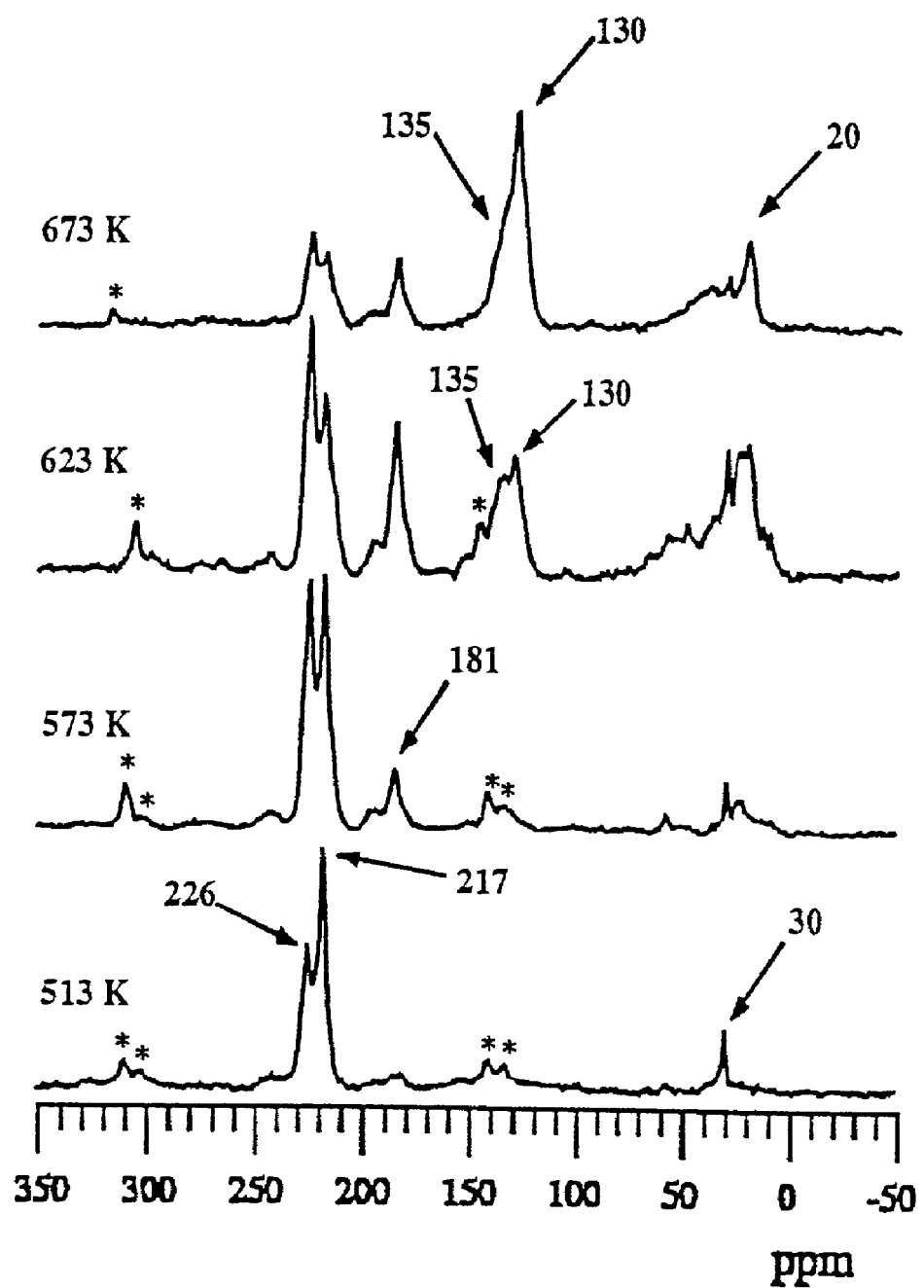

FIG. 13. 75.4 MHz $^{13}$C CP/MAS NMR spectra from pulse-quench studies of acetone-2-$^{13}$C on HSAPO-34. In each case a fresh catalyst bed (ca. 300 mg) was activated in place and then equilibrated at one of the temperatures shown on the figure. 16 mL of acetone-2-$^{13}$C was injected onto the catalyst bed and allowed to react for 4 s in flowing He prior to a rapid thermal quench. All spectra were measured near 298 K. The essential observation is the resolution of the 226 ppm signal from acetone on a stronger acid site from that at 226 ppm for acetone on a weaker site. Aromatics form at higher temperatures. * denotes spinning sideband.

DETAILED DESCRIPTION OF THE PREFERRED EMBODIMENTS

Substantially any solid catalyst that has a microporous structure defined by nanocages may be modified according to the present invention. A "nanocage" is defined herein as a catalyst cage the largest linear dimension of which is about one nanometer and that is accessed through a window that is smaller than the size of the cage.

Suitable catalysts include small pore molecular sieve catalysts including but not necessarily limited to zeolites, silicoaluminophosphates (SAPOs), crystalline metal silicoaluminophosphates (MeAPSO's), crystalline metal aluminophospho oxides (MeAPO's), and aluminophospho oxides (ALPO's). Examples of suitable zeolites include, but are not necessarily limited to ZSM-34, erionite, and chabazite. Examples of suitable MeAPSOs and MeAPO'S include, but are not necessarily limited to SAPO's and alumino phospho oxides comprising preferably in the range of from about 0.005 to about 0.05 moles of a metal selected from the group consisting of magnesium, zinc, iron, cobalt, nickel, manganese, chromium, and mixtures thereof. Examples of suitable small pore ALPO's include, but are not necessarily limited to ALPO-17, ALPO-20, and ALPO-25. The preparation of such catalysts is well known in the art and is described in U.S. Pat. Nos. 4,554,143; 4,440,871; 4,853,197; 4,793,984; 4,752,651; and 4,310,440, all of which are incorporated herein by reference. Preferred molecular sieve catalysts are SAPOs, such as SAPO-34, SAPO 17, SAPO-18, SAPO-43, and SAPO-44, and others which may be synthesized according to U.S. Pat. No. 4,440,871, incorporated herein by reference, and Zeolites, Vol. 17, pp. 512–522 (1996), incorporated herein by reference. Most preferred catalysts are SAPO-17, SAPO-18, and SAPO-34.

The invention provides ship-in-a-bottle synthesis techniques for modifying catalysts such as disclosed above.

In one embodiment the invention provides a solid catalyst comprising a microporous framework defined by nanocages; and an inorganic compound in at least one of the nanocages, wherein said inorganic compound is a product formed by a reaction of a second inorganic molecule that has a kinetic diameter smaller than the kinetic diameter of the inorganic compound. Preferably, the size of the second inorganic molecule is smaller than the windows for accessing the nanocages but the size of the inorganic compound is larger than said windows. In another embodiment, the solid catalyst is a crystalline silicoaluminophosphate molecular sieve, for example, a SAPO-18, SAPO-34, or a mixture thereof. In a preferred embodiment, the second inorganic molecule is selected from the group consisting of $PH_3$, $SiH_4$, $Si_2H_6$, and $B_2H_6$. The inorganic compound may be selected from the group consisting of phosphoric acid, boric acid, silica, a product of the hydrolysis of $PH_3$, a product of the hydrolysis of $SiH_4$, a product of the hydrolysis of $Si_2H_6$, a product of the hydrolysis of $B_2H_6$, a product of the oxidation of $PH_3$, a product of the oxidation of $SiH_4$, a product of the oxidation of $Si_2H_6$ and a product of the oxidation of $B_2H_6$.

In another embodiment, the invention provides a solid catalyst comprising a microporous framework defined by nanocages; and an inorganic compound in at least one of the nanocages, wherein said inorganic compound is a product formed by a reaction of a second inorganic molecule that has a kinetic diameter smaller than the kinetic diameter of the inorganic compound and wherein said at least one of the nanocages has been modified by reaction with the inorganic compound. Preferably, the kinetic diameter of the second inorganic molecule is less than the largest dimension of the windows for accessing the nanocages but the kinetic diameter of the inorganic compound is greater than the largest dimension of said windows. In one embodiment, the solid catalyst is a crystalline silicoaluminophosphate molecular sieve, for example, SAPO-18, SAPO-34, or a mixture thereof. In a preferred embodiment, the second inorganic molecule is selected from the group consisting of $PH_3$, $SiH_4$, $Si_2H_6$, and $B_2H_6$. The inorganic compound may be selected from the group consisting of phosphoric acid, boric acid, silica, a product of the hydrolysis of $PH_3$, a product of the hydrolysis of $SiH_4$, a product of the hydrolysis of $Si_2H_6$, a product of the hydrolysis of $B_2H_6$, a product of the oxidation of $PH_3$, a product of the oxidation of $SiH_4$, a product of the oxidation of $Si_2H_6$ and a product of the oxidation of $B_2H_6$.

As described in the example below, the invention can be applied to synthesis of olefins from oxygenates. Thus, the invention provides a method for converting an organic starting material including at least one oxygenate to olefins, the method comprising contacting a feed comprising said organic starting material including at least one oxygenate with the catalyst of the invention. Preferably, the invention is applied to MTO conversion. Thus, preferably the organic starting material comprises methanol. Preferably, the method is used to increase the selectivity of ethylene over propylene in the MTO conversion reaction.

EXAMPLE

MTO Conversion

In the conversion of oxygenates to light olefins, it is desirable to maximize the production of ethylene and/or propylene and to minimize the production of undesired by-products, such as methane, ethane, propane, carbon dioxide, hydrogen gas, and $C_4^+$ materials, including aromatics. In one embodiment of the invention, catalysts comprising a silicoaluminophosphate (SAPO) molecular sieve are used to produce the desired products.

SAPO Molecular Sieves as Catalysts

Silicoaluminophosphate molecular sieves are generally classified as being microporous materials having 8, 10, or 12 membered ring structures. These ring structures can have an average pore size ranging from about 3.5–15 angstroms. Preferred are the small pore SAPO molecular sieves having an average pore size ranging from about 3.5 to 5 angstroms. These pore sizes are typical of molecular sieves having 8 membered rings.

In general, silicoaluminophosphate molecular sieves comprise a molecular framework of corner-sharing $SiO_2$, $AlO_2$, and $PO_2$ tetrahedral units. This type of framework is effective in converting various oxygenates into olefin products.

The $PO_2$ tetrahedral units within the framework structure of the molecular sieve of this invention can be provided by a variety of compositions. Examples of these phosphonn-eontaining compositions include phosphoric acid, organic phosphates such as triethyl phosphate, and aluminophosphates. The phosphorus-containing compositions are mixed with reactive silicon and aluminum-contaiing compositions under the appropriate conditions to form the molecular sieve.

The $AlO_2$ tetrahedral units within the framework structure can be provided by a variety of compositions. Examples of these aluminum-containing compositions include aluminum alkoxides such as aluminum isopropoxide, aluminum phosphates, aluminum hydroxide, sodium aluminate, and pseudoboehmite. The aluminum-containing compositions are mixed with reactive silicon and phosphorus-containing compositions under the appropriate conditions to form the molecular sieve.

The $SiO_2$ tetrahedral units within the framework structure can be provided by a variety of compositions. Examples of these silicon-containing compositions include silica sols and silicium alkoxides such as tetra ethyl orthosilicate. The silicon-containing compositions are mixed with reactive aluminum and phosphorus-containing compositions under the appropriate conditions to form the molecular sieve.

Substituted SAPOs can also be used in this invention. These compounds are generally known as MeSAPOs or metal-containing silicoaluminophosphates. The metal can be alkali metal ions (Group IA), alkaline earth metal ions (Group IIA), rare earth ions (Group IIIB, including the lanthanoid elements: lanthanum, cerium, praseodymium, neodymium, samarium, europium, gadolinium, terbium, dysprosium, holmium, erbium, thulium, ytterbium and lutetium; and scandium or yttrium) and the additional transition cations of Groups IVB, VB, VIB, VIIB, VIIIB, and IB.

Preferably, the Me represents atoms such as Zn, Mg, Mn, Co, Ni, Ga, Fe, Ti, Zr, Ge, Sn, and Cr. These atoms can be inserted into the tetrahedral framework through an $MeO_2$ tetrahedral unit. The $MeO_2$ tetrahedral unit carries a net electric charge depending on the valence state of the metal substituent. When the metal component has a valence state of +2, +3, +4, +5, or +6, the net electric charge is -2, -, 0, +1, and +2, respectively. Incorporation of the metal component is typically accomplished by adding the metal component during synthesis of the molecular sieve. However, post-synthesis ion exchange can also be used. See, for example, U.S. Pat. No. 5,962,762, the description of the post-synthesis ion exchange method in which is fully incorporated herein by reference.

Silicoaluminophosphate molecular sieves suitable for the invention include SAPO-5, SAPO-8, SAPO-11, SAPO-16, SAPO-17, SAPO-18, SAPO-20, SAPO-31, SAPO-34, SAPO-35, SAPO-36, SAPO-37, SAPO-40, SAPO-41, SAPO-42, SAPO-44, SAPO-47, SAPO-56, and the metal substituted forms thereof. Preferred are SAPO-1 8, SAPO-34, SAPO-35, SAPO-44, and SAPO-47, particularly SAPO-18 and SAPO-34. The molecular sieves can be used alone or in combination.

The silicoaluminophosphate molecular sieves are synthesized by hydrothermal crystallization methods generally known in the art. See, for example, U.S. Pat. Nos. 4,440,871; 4,861,743; 5,096,684; and 5,126,308 for descriptions of such methods, which are fully incorporated herein by reference. A reaction mixture is formed by mixing together reactive silicon, aluminum and phosphorus components, along with at least one template. Generally the mixture is sealed and heated, preferably under autogenous pressure, to a temperature of at least 100° C., preferably from 100–250° C., until a crystalline product is formed. Formation of the crystalline product can take anywhere from around 2 hours to as much as 2 weeks. In some cases, stirring or seeding with crystalline material will facilitate the formation of the product.

Typically, the molecular sieve product will be formed in solution. It can be recovered by standard means, however, such as by centrifugation or filtration. The product can also be washed, recovered by the same means and dried.

The molecular sieves may be admixed (blended) with other materials. When blended, the resulting composition is typically referred to as a catalyst, with the catalyst comprising the molecular sieve.

Materials which can be blended with the molecular sieve can be various inert or binder materials. These materials include compositions such as kaolin and other clays, various forms of alumina or alumina sol, titania, zirconia, quartz, silica or silica or silica sol, and mixtures thereof. These components are also effective in reducing overall catalyst cost, acting as a thermal sink to assist in heat shielding the catalyst during regeneration, densifying the catalyst and increasing catalyst strength. When blended with inert or binder materials, the amount of molecular sieve which is contained in the final catalyst product ranges from 10 to 90 weight percent, preferably 30 to 70 weight percent. The invention contemplates within its scope molecular sieves blended with inert and/or binder materials.

For MTO catalysis, HSAPO-34 and closely related materials (e.g., those with small amounts of metals in the framework) have recently emerged as the materials of choice, in part because aromatics can not diffuse through the windows in these materials. HSAPO-34 has the CHA topology (6) characterized by cages of ca. 1.0 nm by 0.7 nm diameter that are interconnected through 8-ring windows of ca. 0.38 nm in diameter. Thus, molecules such as methanol, phosphine, ammonia, acetone, and propene may freely diffuse through the framework, but larger molecules, even those with kinetic diameters comparable to those of isobutane or 2-methylpropene, are not adsorbed. During MTO conversion on HSAPO-34 the organic components, i.e., methylbenzenes, self-assemble in the nanometer-size cages during a kinetic induction period, where they must remain until burned out, as even benzene is too large to pass through the 0.38 nm windows connecting adjacent cages.

The CHA family encompasses a large number of distinct materials, differentiated by framework composition. The most simple examples are the aluminosilicate zeolite chabazite (7) and the aluminophosphate $AlPO_4$-34. The topological unit cell contains 36 tetrahedral sites; in the case of $AlPO_4$-34, 18 of which are aluminum and 18 are phosphorus. There are three cages per topological cell. FIG. lB shows an enlarged view of the CHA structure focusing on a single cage and its immediate environment. In a preferred embodiment, the invention provides for functionalizing the interior of such catalyst cages. While the cages themselves arc ca. 1 nm in size, they arc interconnected, and hence accessed, through much smaller windows, which implies that molecules larger (with molecular size being defined by the molecule's kinetic diameter) than the windows cannot enter the cages. The invention provides for novel ship-in-a-bottle synthesis methods to introduce such large molecules into the cages.

Variations of CHA frameworks are readily prepared with metals such as cobalt (8–10) or nickel (11–14) substitution as a well as with gallium instead of aluminum. (15) One of the preferred materials of the invention, SAPO-34, is a silico-aluminophosphate. (16) Partial substitution of silicon for phosphorous introduces anion sites into the framework requiring cations in the cages for charge balance. In an exemplary embodiment, SAPO-34 is synthesized through a procedure (17) that yields a material with one tetraethylammonium cation (the template) in each cage. Calcination of the as-synthesized material is achieved by heating in air at 600° C. This burns the template out leaving the catalyst in the acid form. The acid form of this material is denoted as HSAPO-34.

SAPO-34 can also be prepared with two acid sites per cage by using morpholine, a cyclic, secondary amine. (18–20) There is no generally accepted, compact nomenclature for differentiating these two materials. In this patent H$_2$SAPO-34 is used to explicitly refer to materials prepared so as to have two acid sites per cage.

The invention, in a preferred embodiment, is concerned with the functionalization of the nanocages of SAPO-34, largely through reactions at the acid site, and for the purpose of modifying acid catalyzed reactions. In this regard, HSAPO-34 and H$_2$SAPO-34 will potentially have very different properties. For example, it may be possible to functionalize H$_2$SAPO-34 to replace one and only one acid site per cage with a bulky, thermally stable group, leaving the other site available for catalysis in a more constrained environment. An analogous functionalization of HSAPO-34 could titrate every acid site, providing a material with the desired constraints but no acid function.

Roles for Molecules in the Cages of SAPO-34

Figure 2:
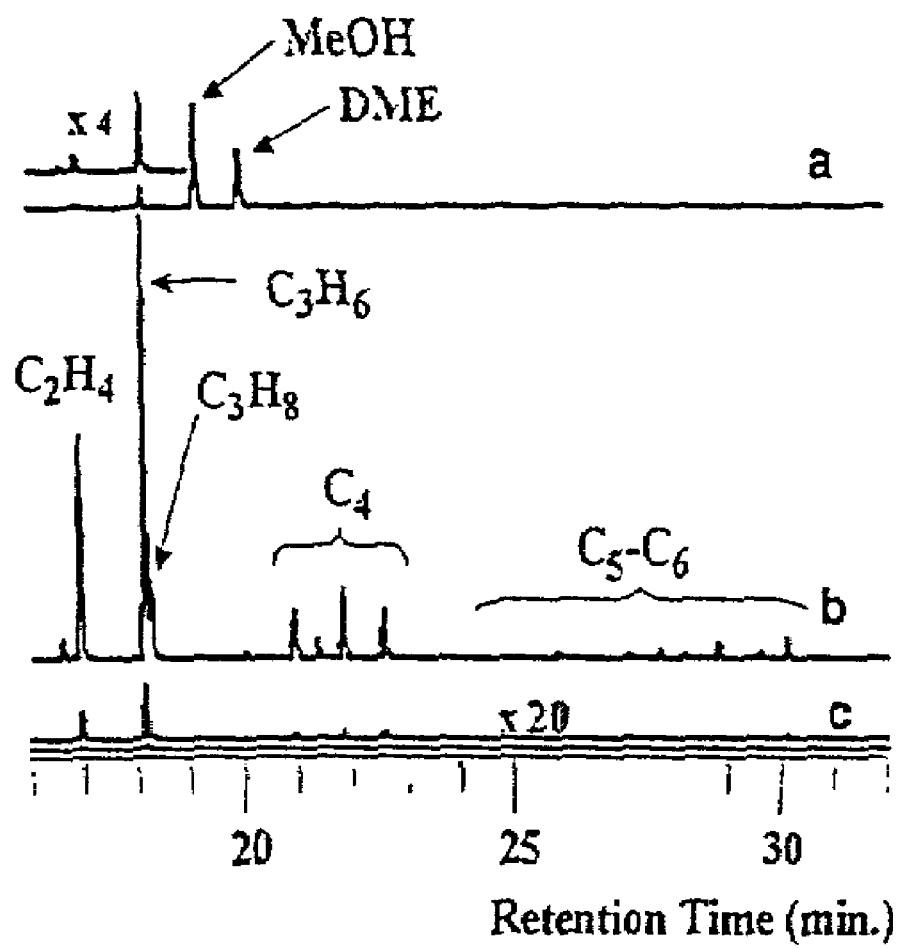
FIG. 2. GC (flame ionization) analyses of the product gases in MTO experiments on HSAPO-34. Identical, 20 mL methanol pulses were applied at 0 s and at 360 s to the same catalyst bed: (a) 4 s after a first pulse the total conversion of methanol and dimethylether (DME) to hydrocarbons was only ca. 14%. (b) 364 s after the first pulse and 4 s after the second pulse, the conversion was essentially 100%. (c) This control experiment, on a second catalyst bed shows that only traces of products exit the reactor 358 s after the first methanol pulse; hence, the products observed at 364 s reflect conversion of the second methanol pulse. Note that even an active catalyst produces more propene than ethylene. It is desirable to increase ethylene selectivity.

FIG. 2 reports gas chromatographic traces (21) that illustrate MTO catalysis on HSAPO-34. For each case illustrated in FIG. 2, methanol was pulsed onto a bed of HSAPO-34 at 450° C. in a flowing stream of He, and a gas sample from the product stream was taken automatically at a certain time and injected onto the column. FIG. 2a shows the result of pulsing methanol onto a freshly activated (i.e., organic-free) catalyst bed and then sampling the product stream 4 s later; the conversion of methanol to olefinic products is poor-only 14%. As FIG. 2b shows, when a second methanol pulse is injected onto the same catalyst bed 360 s after the first, the conversion goes to 100%. FIG. 2c is a control experiment that shows that the products leaving the reactor 360 s after a first pulse are negligible.

Figure 3:
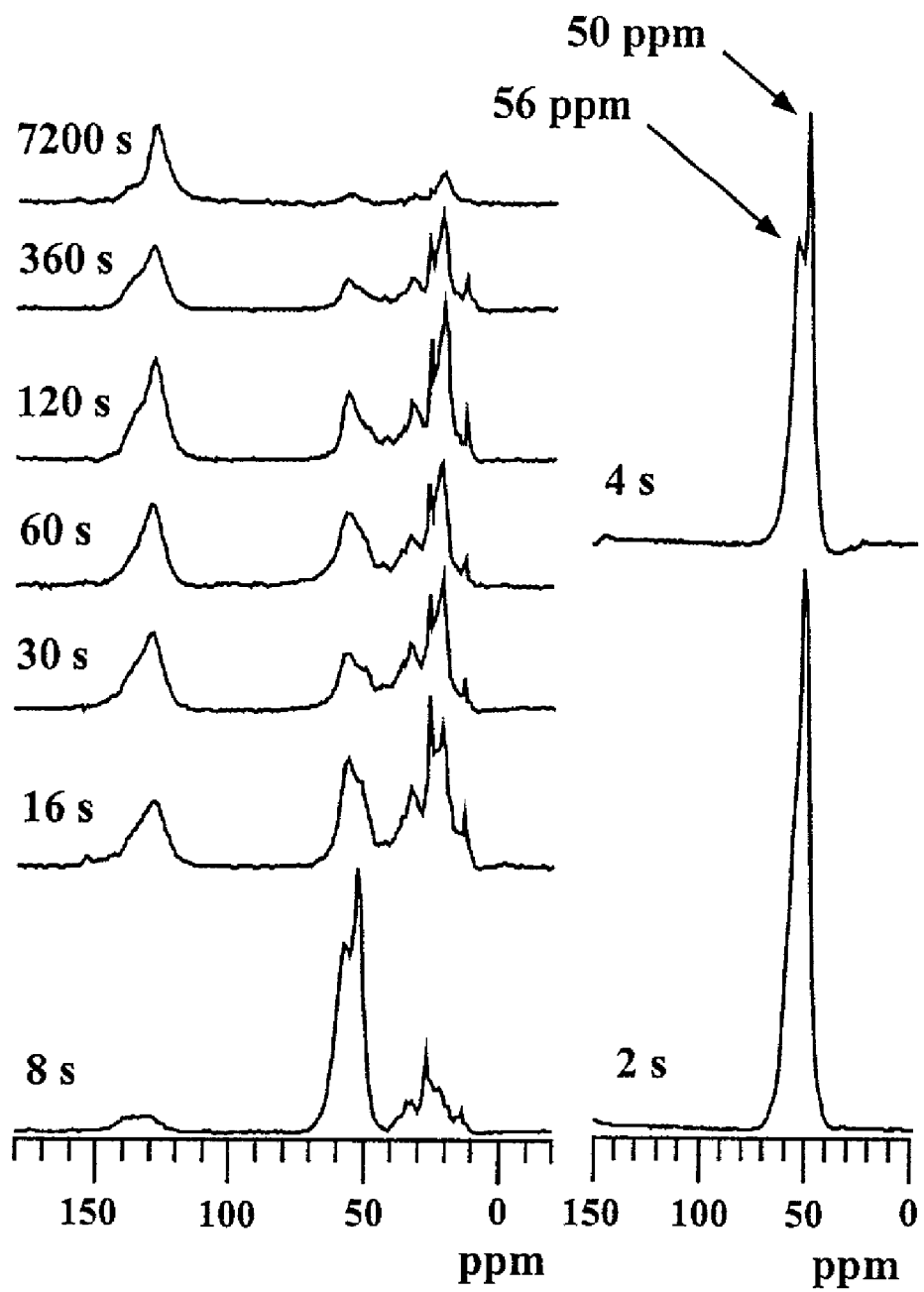
FIG. 3. 75 MHz $^{13}$C CP/MAS NMR spectra of samples from a pulse-quench study of methanol conversion on HSAPO-34 at 673 K. Each sample was prepared by injecting 20 mL of methanol-$^{13}$C onto a freshly activated catalyst bed (0.3 g) while He was flowed at 600 mLmin-1, and reaction occurred for the times shown followed by a rapid thermal quench. All spectra (4000 scans) were measured at 298 K using a 2-ms contact time. Methylbenzenes form as signaled by resonances at 129 ppm to 134 ppm and methyl groups at 20 ppm. The 56 ppm resonance is due to framework bound methoxy (methoxonium) groups.

Mass balance shows that much of the carbon from the first pulse remains on the catalyst. The organic species on the catalyst were characterized by preparing a series of catalysts using the pulse-quench method. (21–25) Briefly, a series of HSAPO-34 catalyst beds were activated, and onto each fresh catalyst a single pulse of methanol was injected, allowed to react for a variable time, and then the temperature of the catalyst bed was rapidly (ca. 200 ms) quenched by flowing onto it a large volume of cryogenically cooled nitrogen gas. Quenched catalyst beds were opened in a nitrogen glove box, transferred to air-tight magic-angle NMR rotors, and $^{13}$C solid state NMR spectra were measured at room temperature. These spectra are shown in FIG. 3. (21) After 4 s of reaction there is a dramatic reduction in the amount of methanol on the catalyst and methyl-substituted aromatics form as signaled by the aromatic resonance at 129 ppm (with a shoulder at 134 ppm due to substituted ring carbons) and methyl groups at 20 ppm. Other upfield signals are accounted for by alkane products trapped in the cages. The average number of methyl groups per ring reaches a maximum of ca. 4 between 30 and 120 s of reaction, but this decreases to ca. 1.4 after the catalyst ages for 7200 s at 673 K without injection of additional feed.

HSAPO-34 catalysts that are active for MTO chemistry have methylbenzenes trapped in their nanocages that self-assemble there. GC-MS shows that when a first pulse is methanol-$^{13}$C and the second pulse is methanol-$^{12}$C, the predominant isotopomer of ethylene in the product stream has one carbon of each isotope. This is evidence that olefin synthesis occurs by methylation of these methylbenzenes. Without intending to be bound by any theory, the mechanism probably involves side-chain alkylation to form ethyl and propyl (or isopropyl) chains, followed by olefin elimination. Alternatively, highly methylated benzenes can rearrange to extend alkyl chains. Either way these species generate the primary olefinic products.

Thus, the active site for olefin synthesis on HSAPO-34 is a composite of an organic species and an inorganic acid site, which can activate methanol and hold methyl cation equivalents. All of this takes place in a nanocage that preserves the organic component and regulates selectivity through steric constraints. The HSAPO-34 active site, then, is no less elegant than those praised in enzyme chemistry.

Nano-Functionaization of HSAPO-34

The following example describes a catalyst that delivers higher ethylene selectivity than standard HSAPO-34, which, in accordance with the invention, was made by a rational process of functionalizing the nanocages.

Figure 4:
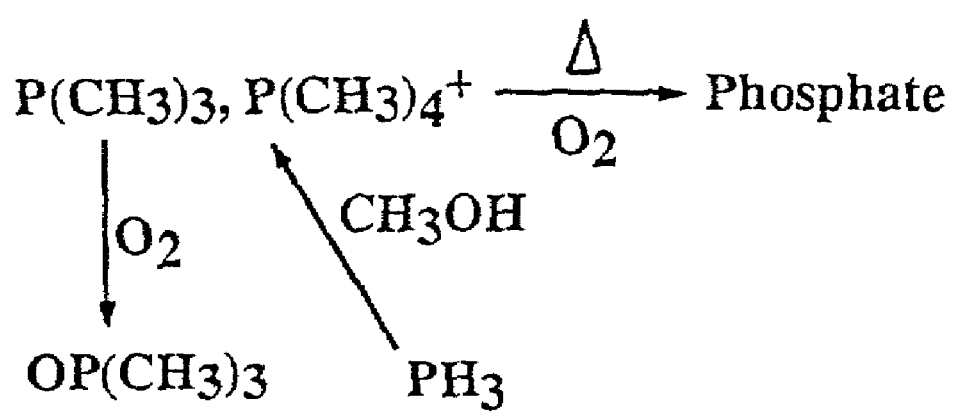
FIG. 4. A scheme for nanocage functionalization based on phosphorus chemistry. All of this chemistry has been achieved in preliminary work, and several examples are reported in FIG. 5.
Figure 5:
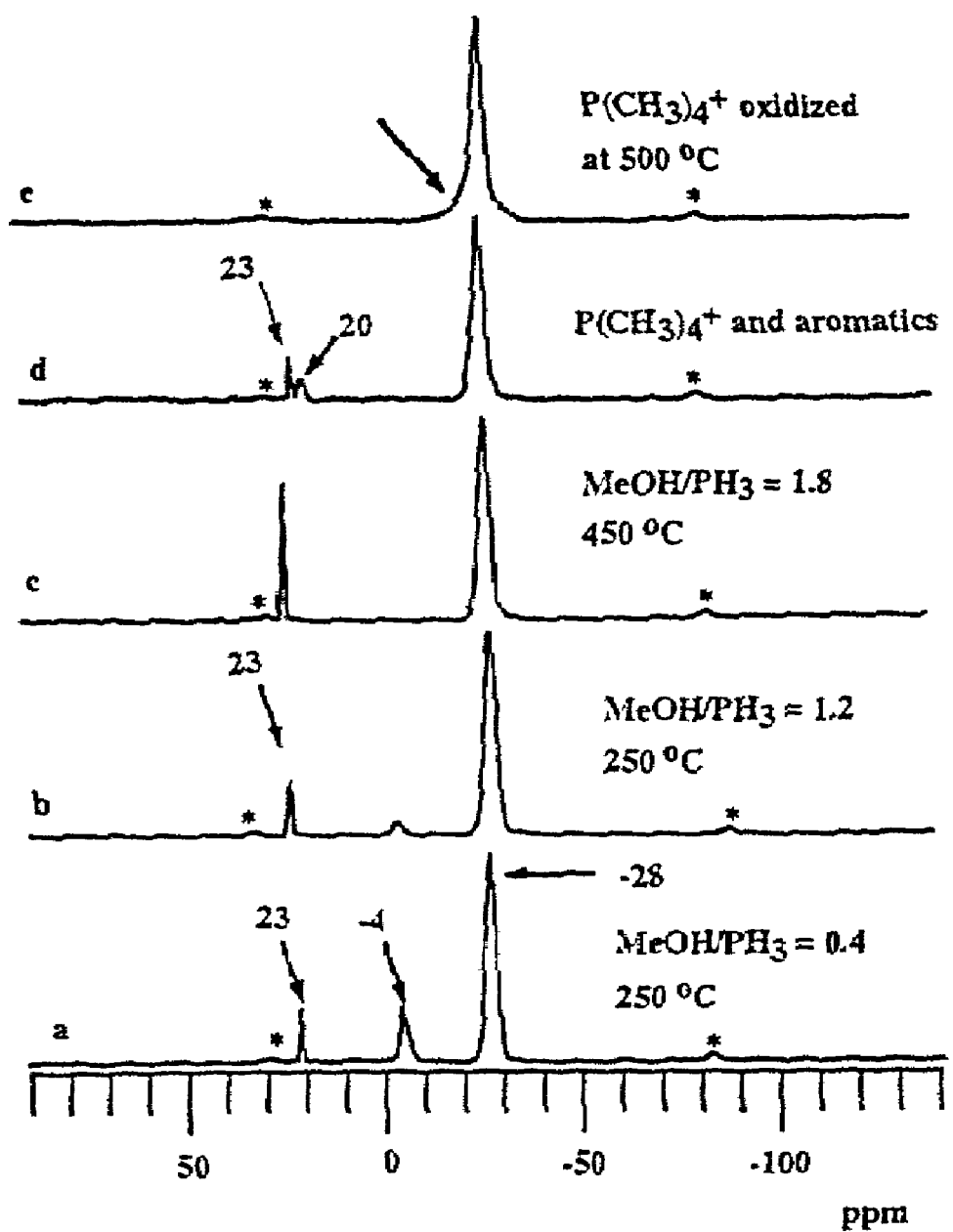
FIG. 5. $^{31}$P MAS NMR spectra showing functionalization of the HSAPO-34 nanocages according to the Scheme, The chemical shift of phosphorus in the HSAPO-34 framework is −26 ppm. In all cases PH$_3$ was flowed over the catalyst bed along with methanol for 10 min. The PH$_3$ flow rate was 14 sccm except for the sample in c where 32 scorn was used. Methanol/PH$_3$ mole ratios are shown on the figure. (a) Wit a limiting amount of methanol the major product in the nanocages was P(CH$_3$)$_3$, which was protonated by the Bransted acid sites (−4 ppm). (b) P(CH$_3$)$_4$$^+$ (23 ppm) formed almost quantitatively in most nanocages when methanol was in excess. (c) Wit forcing conditions, P(CH$_3$)$_4$ $_+$ formed in every cage. (d) P(CH$_3$)$_4$$^+$ yields signals at both 23 ppm and 20 ppm when ca. one-half of the nanocages also contain aroniatics synthesized from methanol. (e) If P(CH$_3$)$_4$$^+$ is formed in the nanocages and the catalyst is heated to high temperatures in air, a phosphate species forms, as indicated by the broad signal near that of the framework. * denotes spinning sidebands.

FIG. 4 presents a reaction scheme for modification of HSAPO-34 by incorporation of various phosphorous species derived from PH$_3$. Phosphine is a very reactive, toxic compound, but it is volatile and small enough to pass through the 0.38 nm windows that interconnect nano-cages. Neither PH$_2$(CH$_3$) nor PH(CH$_3$)$_2$ are commercially available, and P(CH$_3$)$_3$ is too large for absorption. FIG. 5 shows $^{31}$P solid state NMR spectra of SAPO-34 catalysts modified by the reactions in FIG. 4. In each case, the $^{31}$P resonance at -28 ppm is due to phosphorous in the framework. The ratio of P(CH$_3$)$_3$ (~4 ppm) and P(CH$_3$)$_4^+$ (23 ppm) in the cages can be controlled by varying the ratio of PH$_3$ to CH$_3$OH introduced into the flow reactor at 250° C. FIG. 5 also shows a $^{31}$ spectrum of a SAPO-34 containing both P(CH$_3$)$^{4+}$ and aromatics. Note that there are two P(CH$_3$)$_4^+$ resonances, one as before at 23 ppm, but with aromatics present there is also a second peak at 20 ppm. This second peak is almost certainly from cages that contain both P(CH$_3$)$_4^+$ and an aromatic ring, and the upfield shift suggests that the cation is above the plane of the aromatic ring. With sufficient PH$_3$ one P(CH$_3$)$_4^+$ cation in every nano-cage could be synthesized, and the $^{31}$P spectrum then shows a perfect 5:1 ratio of framework to cation signals. When P(CH$_3$)$_4^+$ is heated to 600° C. in SAPO-34, it decomposes to an inorganic phosphate species and at even higher temperatures this appears to react with the framework to yield a material that has been only partially characterized.

Figure 6:
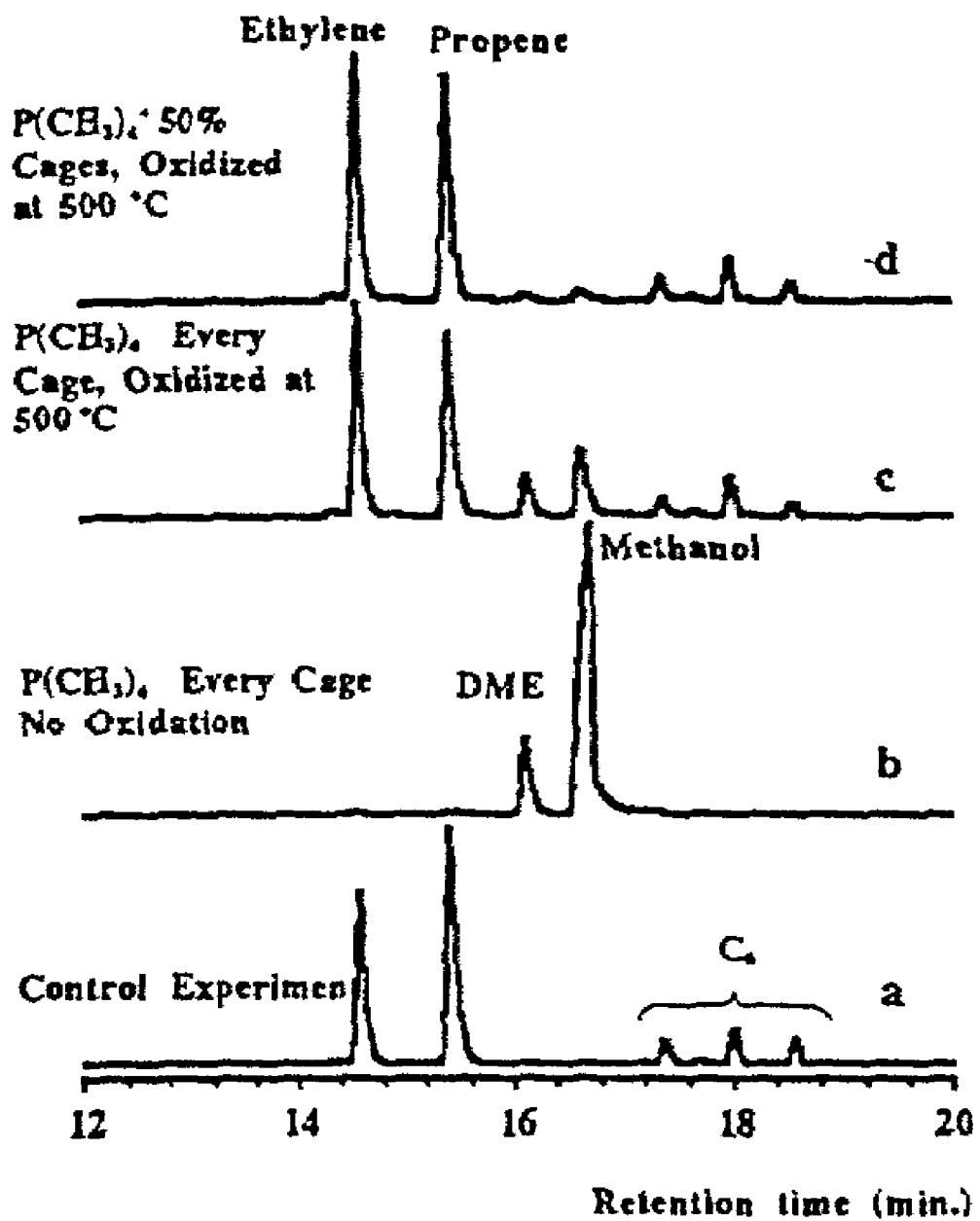
FIG. 6. GC (flame ionization) analyses of the product gases in MTO conversion on catalysts functionalized by introducing phosnhorus species into the nanocages. All experiments at 450° C. and WHSV=8h$^{-1}$. A. Control experiment on standard HSAPO-34; 100% conversion, ethylene selectivity=37%. B. Modified catalysts with P(CH$_3$)$_4$$^+$ in all nanocages; 0% conversion. C. Modified catalyst with phosphate formed in every nanocage by air oxidation (500° C.) of P(CH$_3$)$_4$$^+$; 60% conversion, ethylene selectivity=46%. D. Modified catalyst with H$_3$PO$_4$ formed in ca. 50% of all nanocages by air oxidation (500° C.) of P(CH$_3$)$_4$$^+$; 95% conversion, ethylene selectivity 44%. Note that catalyst D has nearly the same conversion as the standard catalyst, but a significantly higher ethylene selectivity.

FIG. 6 reports GC traces from the product streams of reactors converting methanol under steady-state conditions (WHSV=8 h$^{-1}$) at 450° C. using either standard HSAPO-34 or functionalized materials. With the standard catalyst, conversion was 100% and ethylene selectivity was 37%. Using a material with one P(CH$_3$)$_4$+cation in every cage, conversion was near zero, because the acid sites were removed by phosphonium formation. Calcination of this sample in the reactor to form a material with phosphate in every cage (or a reaction product thereof) produced a catalyst with greatly improved ethylene selectivity, 46%, but slightly reduced activity. When a material with phosphate in most but not all cages was prepared, the catalyst achieved nearly 100% conversion and retained an impressive ethylene selectivity of 44%.

This example demonstrates a scheme for functionalizing SAPO-34 nano-cages to realize desired changes in product selectivity. Such a scheme is easily implemented to achieve any desired functionality in the nanocages. The selection of phosphate acid as a modifier is based on analogous efforts to modify zeolite HZSM-5, which is straightforward due to the 0.55 nm channels of that zeolite. It appears that phosphate functionalized HSAPO-34 has a higher ethylene selectivity because of steno constraints on intermediates and transition states leading to larger olefins in the mare-crowded nanocages of the modified catalyst. These effects can also be achieved by the introduction of other functionalities into the nanocages. Thus, in various exemplary embodiments the invention provides for introducing functionalities created by the reaction within or with the nanocages of an inorganic molecule that is selected from the group consisting of $PH_3$, $SiH_4$, $Si_2H_6$, and $B_2H_6$. Such a reaction product may be selected from the group consisting of phosphoric acid, boric acid, silica, a product of the hydrolysis of $PH_3$, a product of the hydrolysis of $SiH_4$, a product of the hydrolysis of $Si_2H_6$, a product of the hydrolysis of $B_2H_6$, a product of the oxidation of $PH_3$, a product of the oxidation of $SiH_4$, a product of the oxidation of $Si_2H_4$ and a product of the oxidation of $B_2H_6$ and a product of any of the foregoing compounds with a nanocage.

Relationship of Structure to Selectivity of MTO Kinetics

The following "pulse-quench NMR" experiments demonstrate a connection between structure and selectivity and provide further details on MTO kinetics. In pulse-quench experiments, pulses of reagents are injected (commonly stable isotope chemicals) onto a catalyst sample in a flow reactor at some high temperature, which is abruptly (200 ms) reduced to near ambient following a predetermined reaction time. GC or GC-MS is used to analyze the volatile products captured at various times in the reaction, and solid state NMR probes the composition of the quenched catalyst.

As discussed more fully below, by correlating the time evolution of the catalysts' $^{13}C$ NMR spectra and the volatile product distribution following abrupt cessation of methanol flow, it was discovered that (in the absence of other adsorbates) propene is favored by methylbenzenes with four to six methyl groups but ethylene is predominant from those with two or three methyl groups. Ethylene selectivity is substantially increased by operating at lower methanol partial pressures or higher temperatures, either of which reduces the steady-state average methyl substitution. As a step toward a kinetic analysis of the MTO reaction on HSAPO-34, each nanocage was treated with a methylbenzene molecule as a supramolecule capable of unimolecular dissociation into ethylene or propene and a less highly substituted methylbenzene. Addition of a water molecule to a nanocage containing a methylbenzene produces a distinct supramolecule with unique properties. Indeed, co-feeding water with methanol significantly increases the average number of methyl groups per ring at steady state relative to identical conditions without additional water, and also increases ethylene selectivity.

A series of experiments was carried out in which 0.1 mL of methanol or methanol-$^{13}C$ was first flowed onto a 300 mg bed of pelletized HSAPO-34 at 400° C. at a weight hourly space velocity (WHSV) of 8 h$^{-1}$ before abruptly terminating methanol flow and waiting a variable time before quenching the catalyst temperature to ambient. FIG. 7 reports solid state $^{13}C$ MAS NMR spectra of catalysts prepared using delays from 0 to 60 min. These spectra show an aromatic carbon signal between 129 and 134 ppm, and a methyl group resonance at 20 ppm that drops with increasing delay between methanol cut-off and thermal quench. A small, sharp resonance at 25 ppm is due to isobutane, which like the methylbenzenes, is too large to exit the nanocages.

The $^{13}C$ NMR spectra permit direct measurement of the average number of methyl groups per benzene ring in the catalyst, $Me_{ave}$ (Eq. 1).

$$Me_{ave} = [methyls]/[rings] = \sum_{n=0}^{6} nf_n \quad (1)$$

fn denotes the fractions of rings with n methyl groups. As shown in FIG. 7, $Me_{ave}$ decreased from a nearly full complement of 5.6 immediately after methanol cut-off to 2.1 (e.g., xylenes on average) after 60 min. The last methyl group could be removed only with great difficulty. At 450° C., $Me_{ave}$ was 1.1 after 60 min and 0.2 after 14 h.

Figure 8:
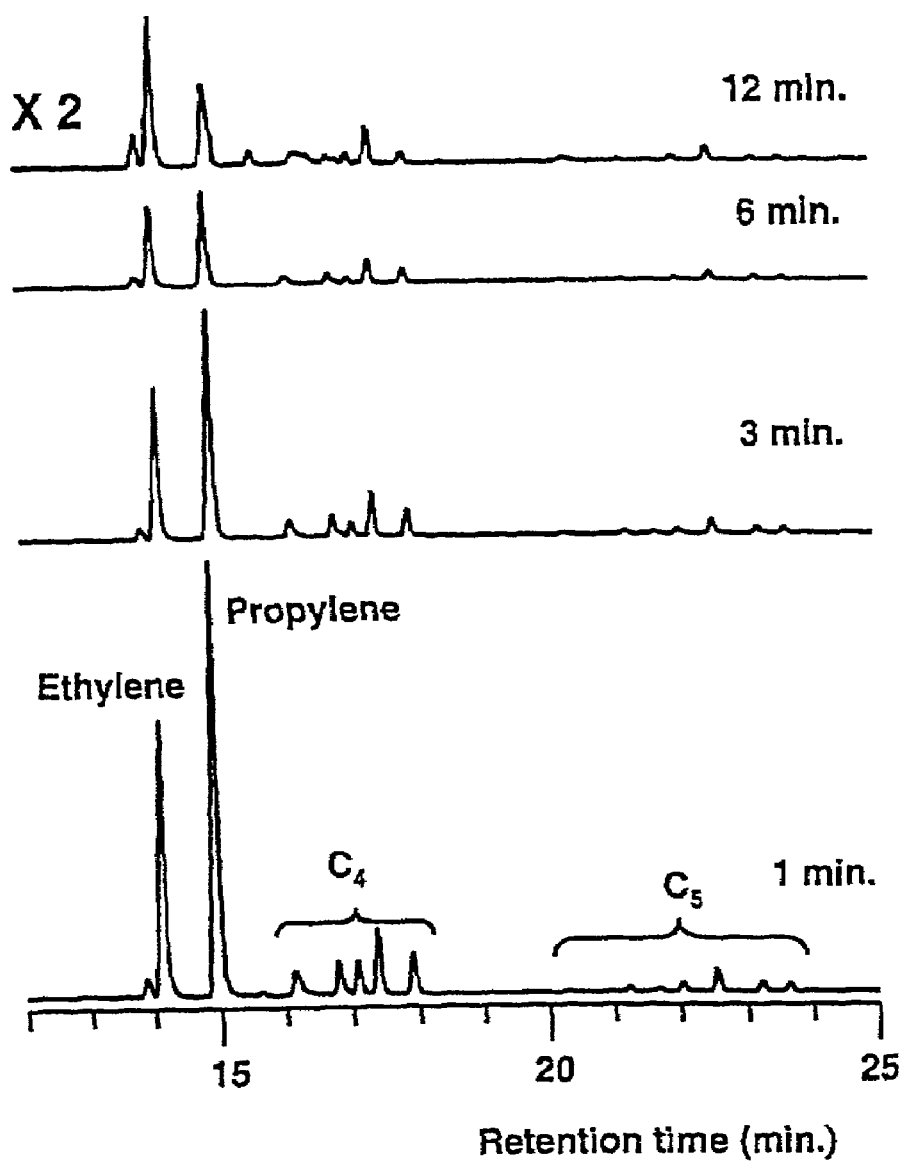
FIG. 8. Gas chromatography (flame-ionization detection) analyses of the volatile products captured immediately prior to thermal quench from the experiments used to prepare some of the samples for FIG. 7. Note the significant increase in ethylene selectivity at longer times. Data were collected using a Hewlett-Packard 6890 gas chromatograph with a Supelco dh150 column operated isothermally at 50° C.
Figures 9A, 9B:
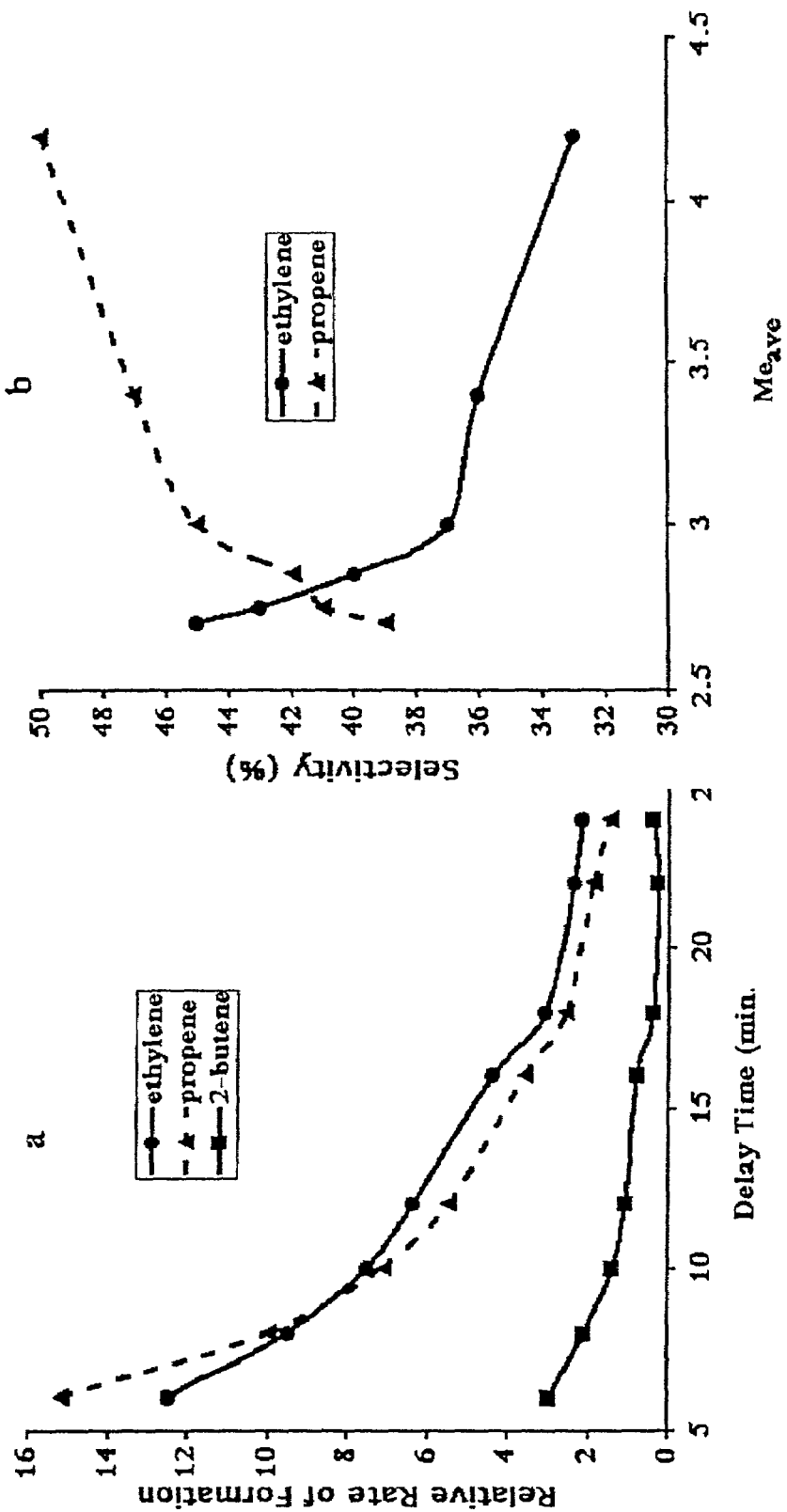
FIG. 9. (A) The rates of formation of ethylene, propylene, and 2-butene as a function of time from a single experiment similar to those used for FIGS. 7 and 8. For these measurements, multiple gas samples were analyzed from a single catalyst bed as it evolved over time after cessation of methanol flow. Ethylene and propylene are primary products of MTO chemistry. It can be shown that C$_4$ products are due to secondary reactions of propylene. (B) Ethylene and propylene selectivity as a function of the average number of methyl groups per ring, Me$_{ave}$. The data in A are re-plotted using an abscissa derived by empirically fitting the time evolution of Me$_{ave}$ in FIG. 7 to a smooth curve generated by Excel. This mapping shows that ethylene is favored by methylbenzenes with 2 or 3 methyl groups, while propylene is favored with four or more methyl groups.

FIG. 8 reports gas chromatographic analyses of samples taken from the product streams immediately prior to thermal quench for several of the experiments used to prepare the samples for FIG. 7. One minute after methanol cut-off, the catalyst was still producing olefinic products with an ethylene selectivity only slightly higher than that immediately prior to cut-off. In particular, at this point the catalyst shows a much higher selectivity for propylene than for ethylene. As the catalyst continued to age at 400° C. with He flow but no further addition of methanol, the total rate of olefin production necessarily fell, but the ethylene selectivity increased dramatically, surpassing that of propylene between 6 and 12 minutes after cut-off. The rates of formation of ethylene, propylene, and a representative $C_4$ product from a single experiment were measured in which a number of gas chromatographic injections were made as a function of time, and these data are plotted in FIG. 9A. Ethylene dominated after 8 min. $C_4$ products arise from secondary reactions and are hereafter neglected. FIG. 9B compares the ethylene and propylene selectivities, computed from FIG. 9A, as a function of the time evolution of the average number of methyl groups per ring-a mapping made possible by a smooth fit of the data in FIG. 7. The data establishes the relationship between molecular structure and selectivity. A change-over in selectivity to ethylene occurs when the number of methyl groups per ring decreased to 2.9, and further decreases in propylene selectivity accompanied further decreases in methyl substitution.

Figures 10A, 10B:
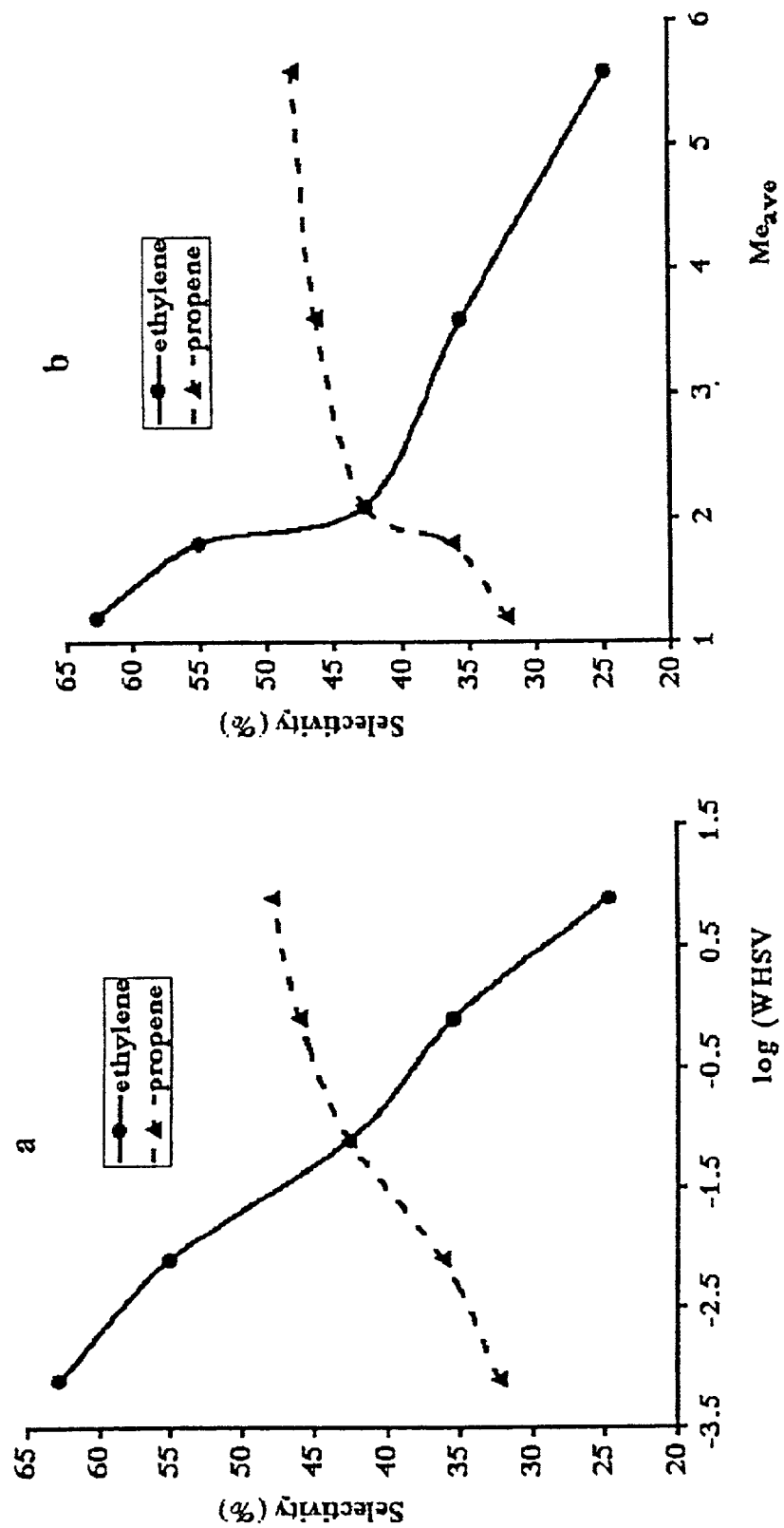
FIG. 10. (A) Ethylene selectivity at 400° C. vs. the logarithm of methanol weight-hourly space velocity. The catalyst bed, 300 mg, was first treated with a total of 0. 1 mL of methanol at WHSV of 8 h$^{-1}$ at 400° C. to create methylbenzenes, and then was held at a given space velocity until selectivity reached a steady-state value. Note the very high ethylene selectivity at very low space velocities.

The following experiment demonstrates the use of rational means for limiting the average number of methyl groups per ring. The methanol space velocity was varied by four orders of magnitude and the steady-state selectivities (all at 400° C. and 100% conversion) reported in FIG. 10A were measured. The ethylene selectivity, which was only 25% at the highest space velocities, increased dramatically as the space velocity was reduced, and steady-state selectivity of 63% at the lowest space velocity was measured. Steady-state values of $Me_{ave}$ were measured at five space velocities using NMR spectra similar to FIG. 7 (0 min delay), and representative examples are shown in FIG. 11. Based on those measurements, FIG. 10B maps the selectivity data in FIG. 4A onto an $Me_{ave}$ coordinate. Under steady-sate conditions, in a catalyst that also contains some methanol and other products in the nanocages, the change-over in selectivity for ethylene vs. propylene occurred at $M_{eave}$=2.1 compared to 2.9 without methanol.

It was also found that for a fixed space velocity of 8 h$^{-1}$, $Me_{ave}$ decreased with increasing temperature, and again this correlated with higher ethylene selectivity. FIG. 11 shows that at 450° C. $Me_{ave}$ was 4.3 (cf. 5.6 at 400° C.) and further dropped to 2.0 at 550° C. The ethylene selectivities were 25% at 400° C., 34% at 450° C., and 50% at 550° C.

The overall kinetics of olefin synthesis on HSAPO-34 are very complicated, and no doubt vary with co-adsorption of methanol, water, or other species into the nano-cages containing the methylaromatics. However, a simplified model can be developed as follows. Consider the simplest case, the cut-off experiments of FIGS. 6 to 8, where the decomposition of methylbenzenes in otherwise empty cages to ethylene or propylene and less-substituted methylbenzenes may be treated as unimolecular dissociation steps. Further, consider the possible reactions of a trimethylbenzene molecule isolated in a nanocage. It is assumed that equilibration of isomers is rapid compared to olefin elimination. Trimethylbenzene can be treated as a single species. Trimethylbenzene can either loose ethylene and leave toluene with a rate constant k3e, or it can instead lose propylene and leave benzene with a rate constant k3p (FIG. 12). If all methylbenzenes function independently, then the decrease in the average number of methyl groups per ring, $Me_{ave}$, in an experiment like FIG. 7 is described by Eq. 2.

$$\frac{d(Me_{ave})}{dt} = \sum_{n=0}^{6} n \frac{df_n}{dt} = \sum_{n=0}^{6} n[-(k_n^e + k_n^p)f_n + k_n^e f_{n+2} + k_n^p f_{n+3}] \quad (2)$$

where $k_0^e = k_0^p = k_1^e = k_1^p = k_2^p = 0$, and $f_i = 0$ when n>6.

FIGS. 7 through 9 allow one to infer the relative values of some of the rate constants. While xylene cannot eliminate propene, $k_2^e$ is not necessarily zero. FIG. 9 shows that the change-over in selectivity at 400° C. occurs with three methyl groups per ring, implying that $k_3^e > k_3^p$. It can be concluded that retention of at least one methyl group on the ring stabilizes transition states leading to olefin elimination. Also, $k_6^p$ is greater than $k_6^e$, and propene is favored at higher space velocities and lower temperatures. Unfortunately, have the following inequalities, $k_6^p > k_3^p$ and $k_6^e > k_3^e$, also exist and the conditions for the most rapid methanol conversion on this catalyst (large $Me_{ave}$) are not those that provide the highest ethylene selectivity (small $Me_{ave}$).

One possibility for nanocage functionalization is to substitute the methylbenzenes with heteroatoms. The rationale for this is that one or more of the steps in detailed mechanisms for reactions as in FIG. 12 must involve the development of charge separation, and functional group substitutents on aromatic rings invariably alter the kinetics of aromatic substitution reactions. For example, phenolic and amino substitutents are activating for electrophilic reactions, while Cl, $CF_3$, etc. are deactivating. A person of ordinary skill in the art can determine with routine experimentation the substituents that would improve catalyst activity or selectivity. In one experiment, phenolic functionality was introduced to existing methylbenzenes in HSAPO-34. This was done using dilute air as an oxidant, though it was also done using a modification of the cumene-hydroperoxide route to phenol. It was found that phenol and catechol rings were no more active than the unreacted benzene rings also present in the catalyst, and there were no obvious changes in selectivity. It is possible that the attempt to realize an activated aromatic ring in a SAPO-34 catalyst was frustrated by pore blockage or some other unanticipated consequence of the partial oxidation reaction, which was carried out near the combustion threshold.

Synthesized Cl and $CF_3$ substituted aromatics were also attempted by more direct ship-in-a-bottle routes (as opposed to post-synthesis functionalization of aromatics). However, these have also proven difficult, in part due to the corrosive effects of acid gases eliminated at high temperatures.

As discussed above, including a bulky species (e.g., $H_3PO_4$) in the HSAPO-34 cage increases ethylene selectivity, presumably by imposing steric constraints on the more bulky transition states leading to propene. An alternate possibility for achieving a similar effect is to use methylnapthalenes instead of methylbenzenes without a second species in the nano-cage. It is known that as HSAPO-34 is deactivated during methanol conversion, (almost) every cage fills with methylnapthalene. (21) Therefore, synthesizing methylnapthalenes in a few of the nano-cages would provide a material with better ethylene selectivity because of the lower free volume in the active cages. Futhermore, even without steric constraints in the cages, each of the two rings in napthalene can bear no more than four methyl substitutents. If "cross-over" of methyl groups from one ring to the next is slow under reaction conditions, the results in FIGS. 7 through 9 show that methylnapthalenes would intrinsically yield higher ethylene selectivities, even without steric constraints.

As discussed above, a material with two acid sites per cage, which we call $H_2SAPO-34$, can be made using morpholine rather than tetraethylammonium as template. $H_2SAPO-34$ has a bad reputation. It is more moisture-sensitive than HSAPO-34, and the higher acid site density promotes secondary reaction leading to $C_4$ and $C_5$ products as well as more rapid deactivation by excessive aromatic formation. However, $H_2SAPO-34$ offers possibilities for nano-functionalization schemes that would not be possible using conventional HSAPO-34. For example, with two acid sites, one and only one could be replaced with a bulky cation, possibly a phosphonium ion as in FIGS. 3 and 4, while leaving the second acid site intact to work with a methylbenzene molecule in the same cage.

With conventional HSAPO-34, all of the acid sites are (ideally) identical, and this is reflected, for example, in a $^1H$ MAS NMR spectrum consisting of a single, sharp line. However, we have found a very small fraction (ca. 2–4%) of sites on the HSAPO-34 materials of the invention to be quite a bit stronger than the majority sites. (40) FIG. 13 shows $^{13}C$ NMR study from a pulse-quench NMR study of the acidity probe acetone-2-$^{13}C$ on HSAPO-34. Most of the acid sites form a complex with a $^{13}C$ isotropic shift of 217 ppm, and this complex is weakly absorbed at high temperatures. For comparison, the aluminosilicate zeolite HZSM-5 induces a larger shift, 223 ppm, in its adsorption complex of acetone.

On the pulse-quench reactor, a second complex, shown by other studies to be present at a few percent of total acid sites, is selectively retained, and yields a resonance at 226 ppm, suggesting a much stronger acid strength. The most plausible explanation for the second site is that it results from over-substitution of silicon into the framework, producing silicious islands with acid strengths closer to those of aluminosilicate zeolites rather than silico-aluminophosphates. Considering each nano-cage to be equivalent may be an oversimplification because a small minority clearly have stronger acid sites than the others. These second type of sites can likely be eliminated through more careful synthetic control.

In the case of $H_2SAPO-34$, there are several non-equivalent ways to create two acid sites per nano-cage. Thus, materials with diverse acid site strengths can be obtained.

Process Details

In a preferred embodiment of the invention, a feed containing an oxygenate is contacted in a reaction zone of a reactor apparatus with the molecular sieve catalyst of the invention at process conditions effective to produce light olefins, i.e., an effective temperature, pressure, WHSV (weight hour space velocity) and, optionally, an effective amount of diluent, correlated to produce light olefins. Usually, the oxygenate feed is contacted with the catalyst when the oxygenate is in a vapor phase. Alternately, the process may be carried out in a liquid or a mixed vapor/liquid phase. When the process is carried out in a liquid phase or a mixed vapor/liquid phase, different conversions and selectivities of feed-to-product may result depending upon the catalyst and reaction conditions.

Olefins can generally be produced at a wide range of temperatures. An effective operating temperature range can be from about 200° C. to 700° C. At the lower end of the temperature range, the formation of the desired olefin products may become markedly slow. At the upper end of the temperature range, the process may not form an optimum amount of i product. An operating temperature of at least 300° C., and up to 500° C. is preferred.

Owing to the nature of the process, it may be desirable to carry out the process of the present invention by use of the molecular sieve catalysts in a dynamic bed system or any system of a variety of transport beds rather than in a fixed bed system.

The conversion of oxygenates to produce light olefins may be carried out in a variety of catalytic reactors, including, but not limited to, fluid bed reactors and concurrent riser reactors as described in "Free Fall Reactor," Fluidization Engineering, D. Kunii and O. Levenspiel, Robert E. Krieger Publishing Co. NY, 1977, incorporated in its entirety herein by reference. Additionally, countercurrent free fall reactors may be used in the conversion process. See, for example, U.S. Pat. No. 4,068,136 and "Riser Reactor", Fluidization and Fluid-Particle Systems, pages 48–59, F. A. Zenz and D. F. Othmo, Reinhold Publishing Corp., NY 1960, the descriptions of which are expressly incorporated herein by reference.

Any standard commercial scale reactor system can be used, including fixed bed or moving bed systems. The commercial scale reactor systems can be operated at a weight hourly space velocity (WHSV) of from 1 hr$^{-1}$ to 1000 h$^{-1}$. In the case of commercial scale reactors, WHSV is defined as the weight of hydrocarbon in the feed per hour per weight of silicoaluminophosphate molecular sieve content of the catalyst. The hydrocarbon content will be oxygenate and any hydrocarbon which may optionally be combined with the oxygenate. The silicoaluminophosphate molecular sieve content is intended to mean only the silicoaluminophosphate molecular sieve portion that is contained within the catalyst. This excludes components such as binders, diluents, inerts, rare earth components, etc.

Preferred reactors are co-current riser reactors and short contact time countercurrent free-fall reactors. In these preferred reactors, an oxygenate feedstock is preferably contacted with a molecular sieve catalyst at a WHSV of at least about 20 hr$^{-1}$, preferably in the range of from about 20 hr$^{-1}$ to 1000 hr$^{-1}$, and most preferably in the range of from about 20 hr$^{-1}$ to 500 hr$^{-1}$.

The pressure also may vary over a wide range, including autogenous pressures. Effective pressures may be in, but are not necessarily limited to, pressures of from about 0.1 kPa to about 4 MPa. Preferred pressures are in the range of about 6.9 kPa to about 2 MPa, with the most preferred range being of from about 48 kPa to about 0.34 MPa. The foregoing pressures are exclusive of any oxygen depleted diluent, and thus, refer to the partial pressure of the oxygenate compounds and/or mixtures thereof with feedstock. At the lower and upper end of the foregoing pressure ranges, the rate of selectivity, conversion and/or reaction may not be optimum.

One or more oxygen depleted diluents may be present in the feedstock, for example, in an amount of from 1 to 99 molar percent, based on the total number of moles of all feed and diluent components fed to the reaction zone (or catalyst). Typical diluents include, but are not necessarily limited to, helium, argon, nitrogen, carbon monoxide, carbon dioxide, hydrogen, water, paraffins, alkanes (especially methane, ethane, and propane), alkylenes, aromatic compounds, and mixtures thereof The preferred diluents are water and nitrogen. Water can be injected in either liquid or vapor form.

The process may be carried out in a batch, semi-continuous or continuous fashion. The process can be conducted in a single reaction zone or a number of reaction zones arranged in series or in parallel.

The level of conversion of the oxygenates can be maintained to reduce the level of unwanted by-products. Conversion can also be maintained sufficiently high to avoid the need for commercially unacceptable levels of recycling of unreacted feeds. A reduction in unwanted by-products is seen when conversion moves from 100 mol % to about 98 mol % or less. Recycling up to as much as about 50 mol % of the feed is commercially acceptable. Therefore, conversion levels which achieve both goals are from about 50 mol % to about 98 mol % and, desirably, from about 85 mol % to about 98 mol %. However, it is also acceptable to achieve conversion between 98 mol % and 100 mol % in order to simplify the recycling process. Oxygenate conversion may be maintained at this level using a number of methods familiar to persons of ordinary skill in the art. Examples include, but are not necessarily limited to, adjusting one or more of the following: the reaction temperature; pressure; flow rate (i.e., WHSV); level and degree of catalyst regeneration; amount of catalyst re-circulation; the specific reactor configuration; the feed composition; and other parameters which affect the conversion.

If regeneration is required, the molecular sieve catalyst can be continuously introduced to a regeneration zone where it can be regenerated, such as for example by removing carbonaceous materials or by oxidation in an oxygen containing atmosphere. In a preferred embodiment, the catalyst is subject to a regeneration step by burning off carbonaceous deposits accumulated during the conversion reactions.

The oxygenate feedstock comprises at least one organic compound which contains at least one oxygen atom, such as aliphatic alcohols, ethers, carbonyl compounds (aldehydes, ketones, carboxylic acids, carbonates, esters and the like), and the feedstock may optionally contain at least one compound containing a halide, mercaptan, sulfide, or amine, as long as the optional components do not significantly impede the performance of the catalyst. When the oxygenate is an alcohol, the alcohol can include an aliphatic moiety having from 1 to 10 carbon atoms, more preferably from 1 to 4 carbon atoms. Representative alcohols include but are not necessarily limited to lower straight and branched chain aliphatic alcohols, their unsaturated counterparts and the nitrogen, halogen and sulfur analogues of such. Examples of suitable oxygenate compounds include, but are not limited to: methanol; ethanol; n-propanol; isopropanol; C4–C20 alcohols; methyl ethyl ether; dimethyl ether; diethyl ether; di-isopropyl ether; formaldehyde; dimethyl carbonate; dimethyl ketone; acetic acid; and mixtures thereof. Preferred oxygenate compounds are methanol, dimethyl ether, or a mixture thereof.

The method of making the preferred olefin product in this invention can include the additional step of making these compositions from hydrocarbons such as oil, coal, tar sand, shale, biomass and natural gas. Methods for making the compositions are known in the art. These methods include fermentation to alcohol or ether, making synthesis gas, then converting the synthesis gas to alcohol or ether. Synthesis gas can be produced by known processes such as steam reforming, autothermal reforming and partial oxidation.

One skilled in the art will also appreciate that the olefins produced by the oxygenate-to-olefin conversion reaction of the present invention can be polymerized to form polyolefins, particularly polyethylene and polypropylene.

Processes for forming polyolefins from olefins are known in the art. Catalytic processes are preferred. Particularly preferred are metallocene, Ziegler/Natta and acid catalytic systems. See, for example, U.S. Pat. Nos. 3,258,455; 3,305,538; 3,364,190; 5,892,079; 4,659,685; 4,076,698; 3,645,992; 4,302,565; and 4,243,691, the catalyst and process descriptions of each being expressly incorporated herein by reference. In general, these methods involve contacting the olefin product with a polyolefin-forming catalyst at a pressure and temperature effective to form the polyolefin product.

A preferred olefin-forming catalyst is a metallocene catalyst. The preferred temperature range of operation is between 50 and 240° C. and the reaction can be carried out at low, medium or high pressure. For processes carried out in solution, an inert diluent can be used, and the preferred operating pressure range is between 10 and 150 bars, with a preferred temperature range of between 120 and 230° C. For gas phase processes, it is preferred that the temperature generally be within a range of 60 to 160° C., and that the operating pressure be between 5 and 50 bars.

All of the publications which are cited in the body of the instant specification are hereby incorporated by reference in their entirety.

It is also to be appreciated that the foregoing description of the invention has been presented for purposes of illustration and explanation and is not intended to limit the invention to the precise manner of practice herein. It is to be appreciated therefore, that changes may be made by those skilled in the art without departing from the spirit of the invention and that the scope of the invention should be interpreted with respect to the following claims.

REFERENCES (1) Corma, A. Inorganic Solid Acids and Their Use in Acid-Catalyzed Hydrocarbon Reactions *Chemical Reviews* 1995, 95, 559–614.

(2) Corma, A. From Microporous to Mesoporous Molecular Sieve Materials and Their Use in Catalysis *Chemical Reviews* 1997, 97, 2373–2419.

(3) VanSanten, R. A.; Kramer, G. J. Reactivity Theory of Zeolitic Bronsted Acidic Sites *Chemical Reviews* 1995, 95, 637–660.

(4) Stöcker, M. Methanol-to-Hydrocarbons: Catalytic Materials and Their Behavior *Microporous and Mesoporous Materials* 1999, 29, 3–48.

(5) Keil, F. J. Methanol-to-Hydrocarbons: Process Technology *Microporous and Mesoporous Materials* 1999, 29, 49–66.

(6) International Zeolite Association, Database of Zeolite Structures, http://www.iza-structure.org/databases/

(7) Dahl, I. M.; Mostad, H.; Akporiaye, D.; Wendelbo, R. Structural and Chemical Influences on the MTO Reaction: a Comparison of Chabazite and SAPO-34 as MTO Catalysts *Microporous and Mesoporous Materials* 1999, 29, 185–190.

(8) Kang, M.; Lee, C. T.; Um, M. H. Synthesis and Characteristics of CoAPSO-34s, and Their Catalytic Performance on Methanol Conversion *Journal of Industrial and Engineering Chemistry* 1999, 5, 10–15.

(9) Chen, J. S.; Thomas, J. M. MAPO-18 (M-Mg,Zn,Co)—A New Family of Catalysts for the Conversion of Methanol to Light Olefins *J. Chem. Soc., Chem. Commun.* 1994, 603–604.

(10) Ashtekar, S.; Chilukuri, S. V. V.; Prakash, A. M.; Harendranath, C. S.; Chakrabarty, D. K. Small Pore Aluminum Phosphate Molecular-Sieves With Chabazite Structure—Incorporation of Cobalt in the Structures SAPO-34 and SAPO-44 *J. Phys. Chem.* 1995, 99, 6937–6943.

(11) Inoue, M.; Dhupatemiya, P.; Phatanasri, S.; Inui, T. Synthesis Course of the Ni-SAPO-34 Catalyst for Methanol-to-Olefin Conversion *Microporous and Mesoporous Materials* 1999, 28, 19–24.

(12) Thomas, J. M.; Xu, Y.; Catlow, C. R. A.; Couves, J. W. Synthesis and Characterization of a Catalytically Active Nickel Silicoaluminophosphate Catalyst for the Conversion of Methanol to Ethene *Chem. Mater.* 1991, 3, 667–672.

(13) Kang, M.; Inui, T. Dynamic Reaction Characteristics Affected by Water Molecules During the Methanol to Olefin Conversion on NiAPSO-34 Catalysts *Journal of Molecular Catalysis a-Chemical* 1999, 140, 55–63.

(14) Djieugoue, M. A.; Prakash, A. M.; Kevan, L. Catalytic Study of Methanol-to-Olefins Conversion in Four Small-Pore Silicoaluminophosphate Molecular Sieves: Influence of the Structural Type, Nickel Incorporation, Nickel Location, and Nickel Concentration *Journal of Physical Chemistry B* 2000, 104, 6452–6461.

(15) Kang, M.; Lee, C. T. Synthesis of Ga-Incorporated SAPO-34s (GaAPSO-34) and Their Catalytic Performance on Methanol Conversion *Journal of Molecular Catalysis a-Chemical* 1999, 150, 213–222.

(16 a) Wilson, S.; Barger, P. The Characteristics of SAPO-34 Which Influence the Conversion of Methanol to Light Olefins *Microporous and Mesoporous Materials* 1999, 29, 117–126.

(16 b) Dahl, I. M.; Kolboe, S. On the Reaction-Mechanism for Hydrocarbon Formation From Methanol Over SAPO-34 .1. Isotopic Labeling Studies of the Co-Reaction of Ethene and Methanol *J. Catal.* 1994, 149, 458–464.

(16 c) Dahl, I. M.; Kolboe, S. On the Reaction Mechanism for Hydrocarbon Formation From Methanol Over SAPO-34 .2. Isotopic Labeling Studies of the Co-Reaction of Propene and Methanol *J. Catal.* 1996, 161, 304–309.

(17) Lok, B. M.; Messina, C. A.; Patton, R. L.; Gajek, R. T.; Cannan, T. R.; Flanigen, E. M. U.S. Pat. No. 4, 440, 871, 1984. XRD showed a pure crystalline phase with the CHA structure. The product was calcined at 873 K for 10 hours to remove the template agent and pressed into 10–20 mesh pellets. The Brønsted site concentration was determined to be 1.1 mmol/g. In typical experiments 0.3 g of catalyst was activated at 673 K under 200 sccm He flow for 2 h immediately prior to use.

(18) Marchese, L.; Frache, A.; Gianotti, E.; Martra, G.; Causa, M.; Coluccia, S. ALPO-34 and SAPO-34 Synthesized by Using Morpholine as Templating Agent. FTIR and FT-Raman Studies of the Host-Guest and Guest- Guest Interactions Within the Zeolitic Framework *Microporous and Mesoporous Materials* 1999, 30, 145–153.

(19) Prakash, A. M.; Unnikrishnan, S. Synthesis of SAPO-34—High-Silicon Incorporation in the Presence of Morpholine as Template *J. Chem. Soc., Faraday Trans.* 1994, 90, 2291–2296.

(20) Briend, M.; Vomscheid, R.; Peltre, M. J.; Man, P. P.; Barthomeuf, D. Influence of the Choice of the Template on the Short-Term and Long-Term Stability of SAPO-34 Zeolite *J. Phys. Chem.* 1995, 99, 8270–8276.

(21) Song, W.; Haw, J. F.; Nicholas, J. B.; Heneghan, K. Methylbenzenes are the Organic Reaction Centers for Methanol to Olefin Catalysis on HSAPO-34 *J. Am. Chem. Soc.* 2000, 122, 10726–10727.

(22) Haw, J. F.; Goguen, P. W.; Xu, T.; Skloss, T. W.; Song, W. G.; Wang, Z. K. In Situ NMR Investigations of Heterogeneous Catalysis With Samples Prepared Under Standard Reaction Conditions *Angewandte Chemie-International Edition* 1998, 37, 948–949.

(23) Goguen, P. W.; Xu, T.; Barich, D. H.; Skloss, T. W.; Song, W. G.; Wang, Z. K.; Nicholas, J. B.; Haw, J. F. Pulse-Quench Catalytic Reactor Studies Reveal a Carbon-Pool Mechanism in Methanol-to-Gasoline Chemistry on Zeolite HZSM-5 *J. Am. Chem. Soc.* 1998, 120, 2650–2651.

(24) Xu, T.; Barich, D. H.; Goguen, P. W.; Song, W. G.; Wang, Z. K.; Nicholas, J. B.; Haw, J. F. Synthesis of a Benzenium Ion in a Zeolite With Use of a Catalytic Flow Reactor *J. Am. Chem. Soc.* 1998, 120, 4025–4026.

(25) Haw, J. F.; Nicholas, J. B.; Song, W. G.; Deng, F.; Wang, Z. K.; Xu, T.; Heneghan, C. S. Roles for Cyclopentenyl Cations in the Synthesis of Hydrocarbons From Methanol on Zeolite Catalyst HZSM-5 *J. Am. Chem. Soc.* 2000, 122, 4763–4775.

(26) Haw, J. F.; Nicholas, J. B.; Xu, T.; Beck, L. W.; Ferguson, D. B. Physical Organic Chemistry of Solid Acids: Lessons From in Situ Nmr and Theoretical Chemistry *Acc. Chem. Res.* 1996, 29, 259–267.

(27) Nicholas, J. B.; Haw, J. F. The Prediction of Persistent Carbenium Ions in Zeolites *J. Am. Chem. Soc.* 1998,120, 11804–11805.

(28) Nicholas, J. B.; Haw, J. F.; Beck, L. W.; Krawietz, T. R.; Ferguson, D. B. Density-Functional Theoretical and Nmr-Study of Hammett Bases in Acidic Zeolites *J. Am. Chem. Soc.* 1995,117, 12350–12351.

(29) Barich, D. H.; Nicholas, J. B.; Xu, T.; Haw, J. F. Theoretical and Experimental Study of the C-13 Chemical Shift Tensors of Acetone Complexed With Bronsted and Lewis Acids *J. Am. Chem. Soc.* 1998, 120, 12342–12350.

(30) Nicholas, J. B.; Kheir, A. A.; Xu, T.; Krawietz, T. R.; Haw, J. F. Theoretical and Solid-State NMR Study of Acetylene Adsorption on Nano-Sized MgO *J. Am. Chem. Soc.* 1998,120,10471–10481.

(31) Beck, L. W.; Xu, T.; Nicholas, J. B.; Haw, J. F. Kinetic NMR and Density-Functional Study of Benzene H/D Exchange in Zeolites, the Most Simple Aromatic-Substitution *J. Am. Chem. Soc.* 1995,117, 11594–11595.

(32) O'Malley, P. J.; Soscun, H.; Collins, S. J. The True Minimum Energy Structure of $H_3SiOHAlH_3$—Implications for Conformational Preferences of Bridged Hydroxyl-Groups in Zeolites *Chem. Phys. Lett.* 1994, 217, 293–295.

(33) Soscun, H.; Hernandez, J.; Castellano, 0. Ab Initio Study of the Topology of the Charge Distribution of $H_3SiO(H)AlH_3$ Conformers *Int. J Quantum Chem.* 2000, 76, 1-9.

(34) Soscun, H.; Hernandez, J.; Castellano, O.; Diaz, G.; Hinchliffe, A. Ab Initio Scf-Mo Study of the Topology of the Charge Distribution of Acid Sites of Zeolites *Int. J. Quantum Chem.* 1998, 70, 951–960.

(35) Nicholas, J. B. Density functional theory studies of zeolite structure, acidity, and reactivity *Top. Catal.* 1997, 4, 157–171.

(36) Stefanovich, E. V.; Truong, T. N. A Simple Method for Incorporating Madelung Field Effects into ab Initio Embedded Cluster Calculations of Crystals and Macromolecules. *J Phys. Chem. B* 1998, 102, 3018–3022.

(37) Hillier, I. H. Chemical reactivity studied by hybrid QM/MM methods. *THEOCHEM* 1999, 463, 45–52.

(38) Benco, L.; Demuth, T.; Hafner, J.; Hutschka, F. Bronsted acid sites in gmelinite. *J. Chem. Phys.* 1999, 111, 7537–7545.

(39) Nicholas, J. B.; Trouw, F, R.; Mertz, J. E.; Iton, L. E.; Hopfinger, A. J. Molecular dynamics simulation of propane and methane in silicalite. *J. Phys. Chem.* 1993, 97, 4149–4163.

(40) Song, W.; Nicholas, J. B.; Haw, J. F. A Persistent Carbenium Ion on the Methanol-to-Olefin Catalyst HSAPO-34: Acetone Shows the Way, *J. Phys. Chem. B.,* 2001, 105, 4317–4323.

What is claimed is:

1. A solid catalyst comprising:
    a microporous framework comprising a silicoaluminophosphate molecular sieve having an average pore size of from about 3.5 to 5 angstroms and defined by nanocages, each such nanocage being accessible through a window that is smaller than the size of the nanocage; and
    an inorganic compound in at least one of the nanocages, wherein said inorganic compound is a product formed within said nanocages by a reaction of an inorganic molecule that has a kinetic diameter smaller than the kinetic diameter of the inorganic compound; and wherein the kinetic diameter of the inorganic molecule is less than the largest linear dimension of windows for accessing said nanocages but the kinetic diameter of the inorganic compound is greater than the largest linear dimension of said windows;
    said catalyst being effective to promote catalytic conversion of from about 50% to 98% of oxygenates in a feedstock to olefins.

2. The solid catalyst of claim 1, wherein the solid catalyst is a crystalline silicoaluminophosphate molecular sieve selected from the group consisting of SAPO-34, SAPO-17, SAPO-18, SAPO-43 and SAPO-44.

3. The solid catalyst of claim 2, wherein the crystalline silicoaluminophosphate molecular sieve is SAPO-18, SAPO-34, or a mixture thereof.

4. The solid catalyst of claim 3, wherein the inorganic molecule is selected from the group consisting of $PH_3$, $SiH_4$, $Si_2H_6$, and $B_2H_4$.

5. The solid catalyst of claim 3, wherein the inorganic compound is selected from the group consisting of phosphoric acid, boric acid, silica, a product of the hydrolysis of $PH_3$, a product of the hydrolysis of $SiH_4$, a product of the hydrolysis of $Si_2H_6$, a product of the hydrolysis of $B_2H_6$, a product of the oxidation of $PH_3$, a product of the oxidation of $SiH_4$, a product of the oxidation of $Si_2I_4$, and a product of the oxidation of $B_2H_6$.

6. A solid catalyst according to claim 1, wherein said at least one of the nanocages has been modified by reaction with the inorganic compound.

7. The solid catalyst of claim 6, wherein the solid catalyst is a crystalline silicoaluminophosphate molecular sieve selected from the group consisting of SAPO-34, SAPO-17, SAPO-18, SAPO-43 and SAPO-44.

8. The solid catalyst of claim 7, wherein the crystalline silicoaluminophosphate molecular sieve is SAPO-18, SAPO-34, or a mixture thereof.

9. The solid catalyst of claim 8, wherein the inorganic molecule is selected from the group consisting of $PH_3$, $SiH_4$, $Si_2H_6$, and $B_2H_6$.

10. The solid catalyst of claim 8, wherein the inorganic compound is selected from the group consisting of phosphoric acid, boric acid, silica, a product of the hydrolysis of $PH_3$, a product of the hydrolysis of $SiH_4$, a product of the hydrolysis of $Si_2H_6$, a product of the hydrolysis of $B_2H_6$, a product of the oxidation of $PH_3$, a product of the oxidation of $SiH_4$, a product of the oxidation of $Si_2H_6$, and a product of the oxidation of $B_2H_6$.

11. The solid catalyst of claim 3, wherein the inorganic molecule is $PH_3$.

12. The solid catalyst of claim 3, wherein the inorganic compound is selected from the group consisting of phosphoric acid, a product of the hydrolysis of $PH_3$, and a product of the oxidation of $PH_3$.

* * * * *